(12) United States Patent
Politino et al.

(10) Patent No.: US 8,222,009 B2
(45) Date of Patent: *Jul. 17, 2012

(54) PROCESS FOR PREPARING DIPEPTIDYL PEPTIDASE IV INHIBITORS AND INTERMEDIATES THEREFOR

(75) Inventors: Michael Politino, Syracuse, NY (US); Matthew M. Cadin, Auburn, NY (US); Paul M. Skonezny, Baldwinsville, NY (US); Jason G. Chen, Manlius, NY (US)

(73) Assignee: Bristol-Myers Squibb Company, Princeton, NJ (US)

(*) Notice: Subject to any disclaimer, the term of this patent is extended or adjusted under 35 U.S.C. 154(b) by 13 days.

This patent is subject to a terminal disclaimer.

(21) Appl. No.: 12/817,370

(22) Filed: Jun. 17, 2010

(65) Prior Publication Data

US 2010/0291642 A1 Nov. 18, 2010

Related U.S. Application Data

(62) Division of application No. 11/104,015, filed on Apr. 12, 2005, now Pat. No. 7,741,082.

(60) Provisional application No. 60/561,986, filed on Apr. 14, 2004.

(51) Int. Cl.
*C12P 13/00* (2006.01)
*C12P 1/00* (2006.01)
*C12N 9/00* (2006.01)
*C12N 9/06* (2006.01)
*C07C 13/28* (2006.01)

(52) U.S. Cl. .......... 435/128; 435/41; 435/183; 435/191; 585/352

(58) Field of Classification Search .................. None
See application file for complete search history.

(56) References Cited

U.S. PATENT DOCUMENTS

| | | | |
|---|---|---|---|
| 6,068,991 A | 5/2000 | Liu et al. | |
| 6,395,767 B2 | 5/2002 | Robl et al. | |
| 7,186,846 B2 | 3/2007 | Sharma et al. | |
| 7,214,702 B2 | 5/2007 | Sharma | |
| 7,223,573 B2 | 5/2007 | Patel et al. | |
| 7,420,079 B2 * | 9/2008 | Vu et al. .................... | 560/155 |
| 2005/0090539 A1 * | 4/2005 | Vu et al. .................... | 514/412 |

FOREIGN PATENT DOCUMENTS

| | | |
|---|---|---|
| EP | 0 808 824 A2 | 11/1997 |
| JP | 10-1998-23896 A | 1/1998 |
| WO | WO 00/04179 | 1/2000 |
| WO | WO 02/14528 A1 | 2/2002 |
| WO | WO 02/053724 A2 | 7/2002 |
| WO | WO 02/081626 A2 | 10/2002 |
| WO | WO 2004/052850 A2 | 6/2004 |
| WO | WO 2004052850 A2 * | 6/2004 |

OTHER PUBLICATIONS

Patel, Ramesh N. "Synthesis of Chiral Pharmaceutical Intermediates by Biocatalysis" Coordination Chemistry Reviews, 2008 (online Nov. 4, 2007), 252 (5-7), pp. 659-701.*
Simpkins, Ligaya M., et al "Potent Non-nitrile Dipeptidic Dipeptidyl Peptidase IV Inhibitors" Bioorg Med Chem Lett. 2007, 17(16), pp. 4487-4490.*

(Continued)

*Primary Examiner* — Chris R Tate
*Assistant Examiner* — Aaron J Kosar
(74) *Attorney, Agent, or Firm* — McDonnell Boehnen Hulbert & Berghoff LLP

(57) ABSTRACT

A process for production of cyclopropyl-fused pyrrolidine-based inhibitors of dipeptidyl peptidase IV is provided which employs a BOC-protected amine of the structure

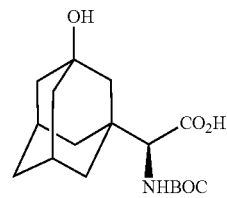

3 prepared by subjecting an acid of the structure

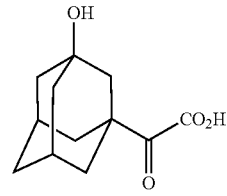

1 to reduce amination by treating the acid with ammonium formate, nicotinamide adenine dinucleotide, dithiothreitol and partially purified phenylalanine dehydrogenase/formate dehydrogenase enzyme concentrate (PDH/FDH) and without isolating treating the resulting amine of the structure 2

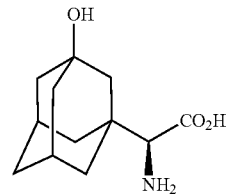

2 with di-tert-butyl dicarbonate to form the BOC-protected amine.

20 Claims, No Drawings

OTHER PUBLICATIONS

Augeri, David J., et al "Discovery and Preclinical Profile of Saxagliptin (BMS-477118): A Highly Potent, Long-Acting, Orally Active Dipeptidyl Peptidase IV Inhibitor for the Treatment of Type 2 Diabetes" J Med Chem, 2005, 48(15), pp. 5025-5037.*

Hanson, RL; Singh, J.; Kissick, T.; Patel, RN.; Szarka, L.; Mueller, R."Synthesis of L-β-hydroxyvaline from α-keto-β-hydroxyisovalerate Using Leucine Dehydrogenase from *Bacillus* species". Bioorganic Chem.,1990,18(2),pp. 116-130 (Abstract only).*

Galkin, Andrey, et al "Synthesis of Optically Active Amino Acids from α-Keto Acids with *Escherichia coli* Cells Expressing Heterologous Genes" Applied and Environmental Microbiology, Dec. 1997,63(12),pp. 4651-4656.*

Patel, RN and Hanson, RL "Synthesis of Chiral Pharmaceutical Intermediates by Oxidoreductases" Applied Biocatalysis in Specialty Chemicals and Pharmaceuticals; Saha, B., et al ed.; ACS Symposium Series, 2001, chapter 15, pp. 216-247.*

Stengelin M. et al.: "Phenylalanine Dehydrogenase Catalyzed Reductive Amination of 6-(1', 3'-Dioxolan-2'-YL)-2-Ketone-Hexanoic Acid to 6-(1', 3'-Dioxolan-2' -YL)-2S-Aminohexanoic Acid With NADH Regeneration and Enzyme and Cofactor Retention," Biocatalysis and Biotransformation, Harwaood Academic Publ., Basel, CH, vol. 18, No. 5, Jan. 1, 2000, pp. 373-400.

Armarego, W.L.F. and Perrin, D.D.: "Purification of Biochemicals and Related Products," Purification of Laboratory Chemicals, 5th ed., 2003, Chapter 6, pp. 500-547.

Armarego, W.L.F. and Perrin, D.D.: "Common Physical Techniques Used in Purification: General Remarks," Purification of Laboratory Chemicals, 4th ed., 2000, Chapter 1, pp. 1-47.

Trager, George. (Drug Delivery Research Department Matrix Pharmaceutical, Inc.(Novartis/Chiron)) Bacteria Cell Lysis, <http://www.bio.net/bionet/mm/methods/1995-February/025062.html> Feb. 25, 1995 (accessed online Sep. 27, 2007) , 1 page.

Jollie, D.R. and Lipscomb, J.D.: "Formate Dehydrogenase from Methylosinus trichosporium OB3b: Purification and Spectroscopic Characterization of the Cofactors," the Journal of Biological Chemistry, 1991, 266(32), pp. 21853-21863.

Asano, Y., Nakazawa, A., Endo, K.: "Novel *Sporosarcina ureae* and *Bacillus sphaericus*: Purification and Characterization," The Journal of Biological Chemistry 1987, 262(21), 10346-10354.

Hanessian, S. et al., "Probing the Importance of Spacial and Conformational Domains in Captopril Analogs for Angiotensin Converting Enzyme Activity," Bioorganic & Medicinal Chemistry Letters, vol. 8, pp. 2123-2128 (1998).

Hanson, R.L. et al.: Synthesis of allys ethylene acetal using phenylalanine dehydrogenase from Thermoactinomyces intetmedius, Enzyme and Microbial Technology, vol. 26, pp. 348-358 (2000).

Imashiro, R. et al.: "Asymmetric synthesis of methyl (2R,3S)-3-(4-methoxyphenyl) glycidate, a key intermediate of diltiazem, via Mukaiya a aldol reaction," Tetrahedron Letters, vol. 42, pp. 1313-1315 (2001).

Reetz, M.T. et al.: "General Synthesis of Potentially Antiviral α-Adamantyl Carbonyl Compounds,"Angew. Chem. Int. Ed. Engl., vol. 18, No. 1, p. 72 (1979).

Reetz, M.T. et al.: "Lewis-Saure-bedingte α-tert-Alkylierung von Carbonsduren und Carbonsdureestern," Chem. Ber., vol. 116, pp. 3708-3724 (1983).

Reetz, M.T. et al.: "Regioselektive Lewis-Sâure-bedingte α-tert-Alkylierung von Acyloinen und Glycolsdure," Chem. Ber., vol. 116, pp. 3702-3707 (1983).

Sagnard, I. et al.: "Enantioselective Synthesis of Cyclopropane a-Amino Acids: Synthesis of N-Boc cis-(2S,3R,4S)-3,4-Methanoproline an N-Boc-(2S,3R,4S)-3,4-Methanoglutamic Acid", Tetrahedron Letters, vol. 36, No. 18, pp. 3148-3152 (1995).

Takada, H. et al.: "Thermostable Phenylalanine Dehydrogenase of Thermoactinomyces intermedius: Cloning, Expression, and Sequencing of Its Gene," J. Biochem., vol. 109, pp. 371-376 (1991).

Tverezovsky, V.V. et al.: "Synthesis of (2S, 3R, 4S)-3,4-Methanoproline and Analogues by Cyclopropylidene Insertion," Tetrahedron, vol. 53, No. 43, pp. 14773-14792 (1997).

* cited by examiner

PROCESS FOR PREPARING DIPEPTIDYL PEPTIDASE IV INHIBITORS AND INTERMEDIATES THEREFOR

This application is a divisional of U.S. application Ser. No. 11/104,015 filed Apr. 12, 2005 which claims the benefit of priority from U.S. Provisional Application No. 60/561,986, filed Apr. 14, 2004, the entire disclosures of which are herein incorporated by reference.

FIELD OF THE INVENTION

The present invention relates to a process for preparing (αS)-α-[[(1,1-dimethylethoxy)carbonyl]-amino]-3-hydroxytricyclo[3.3.1.1$^{3,7}$]decane-1-acetic acid which is employed as an intermediate for preparing cyclopropyl-fused pyrrolidine-based inhibitors of dipeptidyl peptidase IV which are used in the treatment of diabetes and complications thereof, hyperglycemia, Syndrome X, hyperinsulinemia, obesity, and atherosclerosis and related diseases, as well as immunomodulatory diseases and chronic inflammatory bowel disease.

BACKGROUND OF THE INVENTION

Dipeptidyl peptidase IV is a membrane bound non-classical serine aminopeptidase which is located in a variety of tissues including, but not limited to, intestine, liver, lung, and kidney. This enzyme is also located on circulating T-lymphocytes wherein it is referred to as CD-26. Dipeptidyl peptidase IV is responsible for the metabolic cleavage of the endogenous peptides GLP-1(7-36) and glucagons in vivo and has demonstrated proteolytic activity against other peptides such as GHRH, NPY, GLP-2 and VIP in vitro.

GLP-1(7-36) is a 29 amino acid peptide derived from post-translational processing of proglucagon in the small intestine. This peptide has multiple actions in vivo. For example, GLP-1(7-36) stimulates insulin secretion and inhibits glucagon secretion. This peptide promotes satiety and slows gastric emptying. Exogenous administration of GLP-1(7-36) via continuous infusion has been shown to be efficacious in diabetic patients. However, the exogenous peptide is degraded too rapidly for continual therapeutic use.

Inhibitors of dipeptidyl peptidase IV have been developed to potentiate endogenous levels of GLP-1(7,36). U.S. Pat. No. 6,395,767 to Hamann et al. discloses cyclopropyl-fused pyrrolidine-based inhibitors of dipeptidyl peptidase IV. Methods for chemically synthesizing these inhibitors are disclosed in U.S. Pat. No. 6,395,767 as well as in the literature. For example, see Sagnard et al. Tet-Lett. 1995 36:3148-3152; Tverezovsky et al. Tetrahedron 1997 53:14773-14792; and Hanessian et al. Bioorg. Med. Chem. Lett. 1998 8:2123-2128. A preferred inhibitor disclosed in U.S. Pat. No. 6,395,767 is (1S,3 S,5 S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, as depicted in Formula M'.

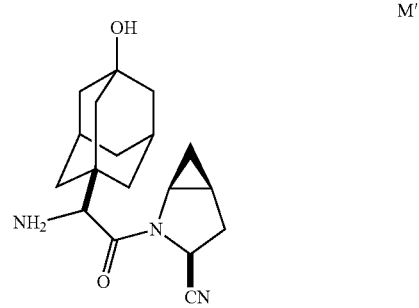

and the corresponding monohydrate of (1S,3S,5S)-2-[(2S)-2-amino-2-(3-hydroxy-tricyclo[3.3.1.1$^{3,7}$]dec-1-yl)-1-oxo-ethyl]-2-azabicyclo-[3.1.0]hexane-3-carbonitrile (M")

Methods adapted for preparing intermediates used in the production of this dipeptidyl peptidase IV inhibitor are disclosed in EP 0 808 824 A2. Also see, Imashiro and Kuroda Tetrahedron Letters 2001 42:1313-1315, Reetz et al. Chem. Int. Ed. Engl. 1979 18:72, Reetz and Heimbach Chem. Ber. 1983 116:3702-3707, Reetz et al. Chem. Ber. 1983 116:3708-3724.

The present invention provides new production methods and compounds for use in the production of cyclopropyl-fused pyrrolidine-based inhibitors of dipeptidyl peptidase IV.

U.S. Pat. No. 6,395,767 to Hamann et al. describes procedures for the synthesis of (αS)-α-[[(1,1-dimethylethoxy)carbonyl]-amino]-3-hydroxytricyclo[3.3.1.1$^{3,7}$]decane-1-acetic acid, an intermediate for use in preparing the free base M' or salt thereof, which involves an eight-step synthesis from adamantane carboxylic acid.

U.S. application Ser. No. 10/716,012 filed Nov. 18, 2003 discloses a method for preparing (αS)-α-[[(1,1-dimethylethoxy)carbonyl]-amino]-3-hydroxytricyclo[3.3.1.1$^{3,7}$]decane-1-acetic acid which utilizes 3-hydroxy-α-oxotricyclo [3.3.1.1$^{3,7}$]-decane-1-acetic acid as a starting material and wherein an enzymatic reductive amination is used to prepare and isolate (αS)-α-amino-3-hydroxytricyclo[3.3.1.1$^{3,7}$]decane-1-acetic acid which is converted to the desired product in a separate step.

The enzymatic reductive amination step involves use of various forms of the enzyme phenylalanine dehydrogenase (PDH) in combination with the enzyme formate dehydrogenase enzyme (FDH) in the presence of ammonium formate, DTT and NAD using ammonium hydroxide for pH adjustment. Where excess ammonium ions are present, it may be necessary to remove ammonia before further downstream processing to avoid possible interference with the introduction of a BOC group.

The cells from which the PDH and/or FDH enzymes are produced are isolated from fermentation broth, stored until ready for use. Before using, the cells are microfluidized to release enzyme from the cells together with the cell debris which must be removed before the enzymes are ready for use in reductive amination.

BRIEF DESCRIPTION OF THE INVENTION

In accordance with the present invention, a process is provided for preparing partially purified phenylalanine dehydrogenase and/or formate dehydrogenase enzyme (PDH/FDH) concentrates which include the steps of:

a. preparing a fermentation broth of a microorganism capable of producing phenylalanine dehydrogenase and/or formate dehydrogenase;

b. subjecting the broth to microfluidization to release activity from the resulting cells and form a microfluidized broth having PDH and/or FDH activity.

c. clarifying the broth by treating the broth with a flocculating agent to coagulate cell debris and remove DNA and unwanted proteins;

d. filtering the clarified broth; and e. concentrating the broth to give a partially purified enzyme concentrate having a PDH/FDH activity of at least about 400 IU/ml for PDH and at least about 20 IU/ml for FDH.

In addition, in accordance with the present invention, a process is provided for preparing an amine of the structure

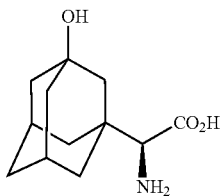

Formula 2 which includes the steps of a. treating an aqueous solution of a keto acid of the structure

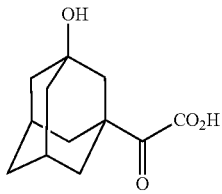

Formula 1 with a maximum of about 2 molar equivalents of ammonium formate, nicotinamide adenine dinucleotide, dithiothreitol and partially purified phenylalanine dehydrogenase/formate dehydrogenase enzyme (PDH/FDH); and b. maintaining the pH of the reaction at from about 7.0 to about 8.6, preferably at 8.0+/−0.2 with sodium hydroxide to form the desired amine which is substantially free of undesirable excess ammonium ions.

Still further in accordance with the present invention, a process is provided for preparing a BOC-protected amine of the structure

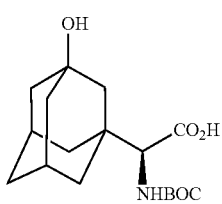

Formula 3 which includes the steps of a. providing an aqueous solution of the amino acid (αS)-α-amino-3-hydroxytricyclo[3.3.1.1$^{3,7}$]decane-1-acetic acid of the structure

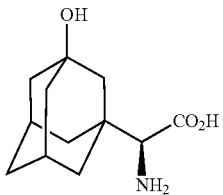

Formula 2

(prepared employing partially purified phenylalanine dehydrogenase/formate dehydrogenase enzymes in the reductive amination of the keto acid 1

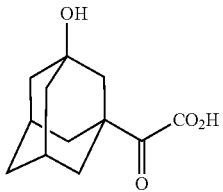

Formula 1 described above); and b. treating the above aqueous solution with di-tert-butyl dicarbonate to form the BOC-protected amine.

In another embodiment of the present invention, a process is provided for preparing the BOC-protected amine of the structure 3

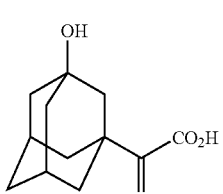

Formula 3 which includes the steps of a. preparing partially purified phenylamine dehydrogenase/formate dehydrogenase enzymes (PDH/FDH) (as described hereinbefore);

b. treating an aqueous solution of a keto acid of the structure 1

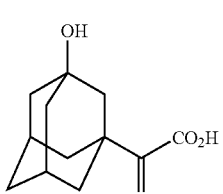

Formula 1 with ammonium formate, nicotinamide adenine dinucleotide, dithiothreitol and the partially purified phenylalanine dehydrogenase/formate dehydrogenase enzymes (PDH/FDH);

c. maintaining the pH of the reaction mixture at from about 7.0 to about 8.6, preferably at 8.0+/−0.2 with sodium hydroxide and forming the desired amine 2

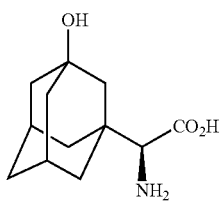

Formula 2 which is substantially free of undesirable excess ammonium ions; and d. without isolating the amino acid intermediate 2, treating the above aqueous solution with di-tert-butyl dicarbonate to form the BOC-protected amine of the structure 3.

The process of the invention provides significantly improved processing procedures by employing partially purified enzymes and employing sodium hydroxide for pH adjustment as opposed to ammonium hydroxide, reduces processing times and allows for isolation of crystalline product without requiring isolation of intermediates. In addition, the process of the invention provides for preparation of partially purified PDH/FDH enzymes employing reaction conditions which allows for a minimum amount of ammonium ions to be present for downstream processing that will not interfere with the introduction of a BOC group. Moreover, use of partially purified PDH/FDH enzyme concentrate in the reductive amination of the Formula 1 acid allows for elimination of the requirement of resin column isolation of the above mentioned amino acid intermediate of Formula 2 after the bioconversion reaction. The reaction stream will be sufficiently clean (free of cell debris and having reduced protein levels) to continue directly with the BOC reaction, and extraction and crystallization of the resulting desired BOC protected intermediate.

In a preferred embodiment, the BOC-protected compound 3 is used as an intermediate in the process of the invention for the production of the dipeptidyl peptidase IV inhibitor (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) as depicted in Formula M

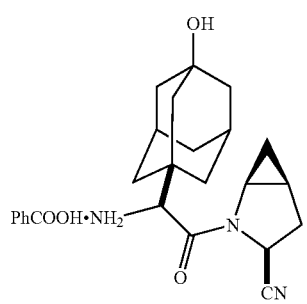

M or its free base M',

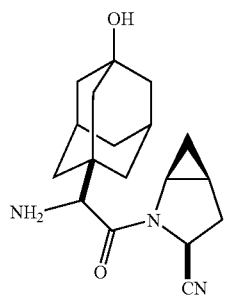

M' and monohydrate M" thereof

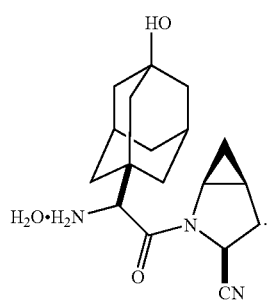

M"

These inhibitors are ultimately formed from the coupling of two fragments, BOC-protected (αS)-α-amino-3-hydroxytricyclo[3.3.1.1$^{3,7}$]decane-1-acetic acid as depicted in Formula 3,

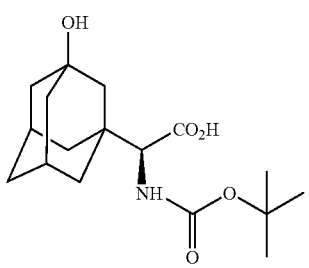

3

(prepared employing the partially purified PDH/FDH enzyme prepared in accordance with the present invention) and (1S,3S,5S)-2-azabicyclo[3.1.0]hexane-3-carboxamide acid salt such as the hydrochloride salt or the methanesulfonic acid salt (mesyl or MSA salt) as depicted in Formula J

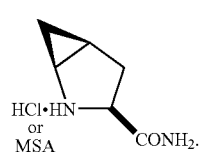

J

Cyclopropyl-fused pyrrolidine-based compounds such as (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) and its corresponding free base and monohydrate thereof are dipeptidyl peptidase IV inhibitors useful in the treatment of diabetes and complications thereof, hyperglycemia, Syndrome X, hyperinsulinemia, obesity, and atherosclerosis and related diseases, as well as immunomodulatory diseases and chronic inflammatory bowel disease. In the present invention, BOC-protected compounds (prepared via a reductive amination process employing partially purified PDH/FDH enzymes in accordance with the present invention) are employed for use in production of cyclopropyl-fused pyrrolidine-based compounds such as (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) and its corresponding free base and monohydrate thereof.

DETAILED DESCRIPTION OF THE INVENTION

In carrying out the preparation of the partially purified PDH/FDH enzyme concentrate of the invention, a microorganism expressing PDH and/or FDH activity is fermented. The fermentation broth will be passed through a microfluidizer operating under a pressure within the range 8000 to about 30,000 psi, preferably from about 12,000 to about 20,000 psi while maintaining the broth at a temperature within the range from about 4° C. to 30° C., preferably from about 8° C. to about 15° C., more preferably below 40° C. The whole broth will be clarified by preferably adding a filter aid to the broth such as diatomaceous earth (for example Dicalite® registered trademark of Grefco Minerals, Inc. and Celite® registered trademark of World Minerals, Inc.) and a flocculating agent such as aqueous polyethyleneimine or other flocculating agent such as heat, to remove DNA and other high molecular proteins. The mixture is then filtered using a filter press and filtrate is recovered. Filter cake is washed with water and the water is recovered and added to the filtrate all of which is referred to as clarified broth.

The clarified broth is ultrafiltered through a 100,000 MWCO (molecular weight cutoff) membrane to remove lower molecular weight (below 100,000) impurities.

The clarified filtrate is concentrated to provide an enzyme concentrate with PDH titer from about 400 to about 1000 IU/ml, preferably from about 500 to about 600 IU/ml, and FDH titer from about 20 to about 200 IU/ml, preferably from about 75 to about 150 IU/ml.

The overall enzyme activity recovery in the concentrate will be within the range from about 65 to about 95%, preferably from about 75 to about 90%.

The term "partially purified" PDH/FDH enzymes as employed herein refers to PDH/FDH enzymes where at least a portion of DNA and other high molecular weight proteins and lower molecular weight impurities have been removed.

In carrying out the reductive amination of 3-hydroxy-α-oxotricyclo[3.3.1.1$^{3,7}$]decane-1-acetic acid (Formula 1 acid), an aqueous mixture of the Formula 1 acid is prepared and the mixture is adjusted to a pH within the range from about 7.0 to about 8.6, preferably from about 7.8 to about 8.2 with strong alkali metal base such as an alkali metal hydroxide, preferably NaOH, to form a solution of Formula 1 acid. Carbon (for example, Darco KB) may be added and the mixture filtered and filtrate and washes combined to give a clear solution.

Ammonium formate is added to the solution in an amount to provide a molar ratio of ammonium formate:Formula 1 acid within the range from about within the range from about 1.9:1 to about 2.5:1, preferably about 2:1. pH of the resulting mixture is adjusted to within the range from about 7.0 to about 8.6, preferably from about 7.8 to about 8.2, employing strong alkali metal base, such as an alkali metal hydroxide, preferably NaOH.

Nicotinamide adenine dinucleotide (NAD) and, optionally, a reducing agent such as dithiothreitol or beta-mercaptoethanol, preferably dithiothreitol are added employing a molar ratio of NAD:Formula 1 acid within the range from about 500:1 to about 1500:1, preferably from about 900:1 to about 1200:1. After solids are dissolved, the partially purified PDH/FDH enzyme concentrate (from about 400 to about 600 IU PDH/gram Formula 1) is added. pH is readjusted to within the range from about 7.0 to about 8.6, preferably from about 7.7 to about 8.2 with strong base such as NaOH.

The mixture is warmed to a temperature within the range from about 25 to 45° C., preferably from about 37 to about 40° C. and diluted with water and the pH maintained with alkali metal base as described above, preferably NaOH, at a pH within the range from about 7.0 to about 8.6, preferably from about 7.8 to about 8.2 over a period to effect reductive amination of Formula 1 acid to form (αS)-α-3-hydroxytricyclo[3.3.1.1$^{3,7}$]decane-1-acetic acid (formula 2 amine).

BOC-protection of the Formula 2 amine is achieved without isolating the Formula 2 amine inasmuch as the amine 2 will be free of cell debris. Di-tert-butyl dicarbonate is added to at least a portion of the solution of Formula 2 amine employing a molar ratio of di-tert-butyl dicarbonate:Formula 2 amine within the range from about 2:1 to about 2.5:1, preferably from about 2.0:1 to about 2.2:1. The pH of the reaction mixture is adjusted to within the range from about 8.5 to about 12.5, preferably from about 9.5 to about 10.5 using a strong base such as NaOH as described above.

The resulting BOC-protected compound (Formula 3) is extracted and recovered and crystallized to form the BOC-protected Formula 3 amine.

As seen above, in one aspect of the present invention, processes are provided for production of the fragment (αS)-α-amino-3-hydroxytricyclo[3.3.1.1$^{3,7}$]decane-1-acetic acid (Formula 2) by reductive amination of the intermediate compound 3-hydroxy-α-oxotricyclo[3.3.1.1$^{3,7}$]decane-1-acetic acid (Formula 1). In a preferred embodiment of this method, 3-hydroxy-α-oxotricyclo[3.3.1.1$^{3,7}$]decane-1-acetic acid (Formula 1) is converted to (αS)-α-amino-3-hydroxytricyclo[3.3.1.1$^{3,7}$]decane-1-acetic acid (Formula 2) by reductive amination performed enzymatically using the partially purified phenylalanine dehydrogenase/formate dehydrogenase enzyme concentrate of the invention as described above. Exemplary phenylalanine dehydrogenases useful in the present invention include, but are not limited to, those from *Sporosarcina* species or a phenylalanine dehydrogenase from *Thermoactinomyces* species such as *Thermoactinomyces intermedius*. It is preferred that reductive amination be performed with the phenylalanine dehydrogenase of *Thermoactinomyces intermedius*, ATCC 33205, expressed in *Escherichia coli* or *Pichia pastoris*. Construction and growth of recombinant strains of *E. coli* and *Pichia pastoris* expressing phenylalanine dehydrogenase *Thermoactinomyces intermedius*, ATCC 33205, have been described by Hanson et al. (Enzyme and Microbial Technology 2000 26:348-358). Growth of *Pichia pastoris* on methanol also induces the production of formate dehydrogenase (Hanson et al. Enzyme and Microbial Technology 2000 26:348-358).

*E. coli* cells containing a plasmid expressing the *Pichia pastoris* (ATCC 20864) formate dehydrogenase and a modified version of the *Thermoactinomyces intermedius* (ATCC 33205) phenylalanine dehydrogenase gene were deposited and accepted by an International Depository Authority under the provisions of the Budapest Treaty. The deposit was made on Jun. 25, 2002 to the American Type Culture Collection at 10801 University Boulevard in Manassas, Va. 20110-2209. The ATCC Accession Number is PTA-4520. All restrictions upon public access to this cell line will be irrevocably removed upon granting of this patent application. The Deposit will be maintained in a public depository for a period of thirty years after the date of deposit or five years after the last request for a sample or for the enforceable life of the patent, whichever is longer. The above-referenced cell line was viable at the time of the deposit. The Deposit will be replaced if viable samples cannot be dispensed by the depository.

Most preferred is the phenylalanine hydrogenase of *Escherichia coli* JM110 containing a plasmid pBMS-2000-PPFDH-PDH mod. expressing the *Pichia pastoris* (ATCC 20864) formate dehydrogenase and a modified version of the *Thermoactinomyces intermedius* (ATCC 33205) phenylalamine dehydrogenase.

Reductive amination of 3-hydroxy-α-oxotricyclo[3.3.1.1$^{3,7}$]decane-1-acetic acid (Formula 1) to (αS)-α-amino-3-hydroxytricyclo[3.3.1.1$^{3,7}$]decane-1-acetic acid (Formula 2) is depicted in the following Scheme I:

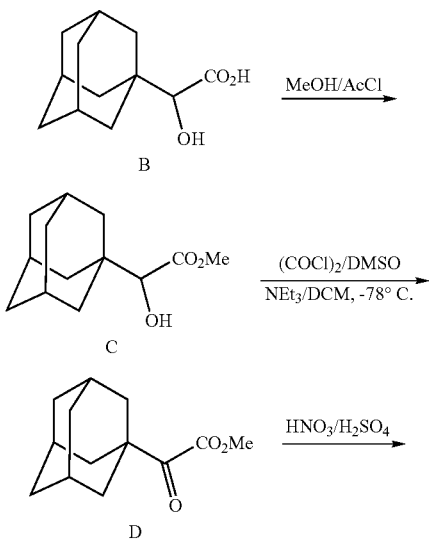

SCHEME I

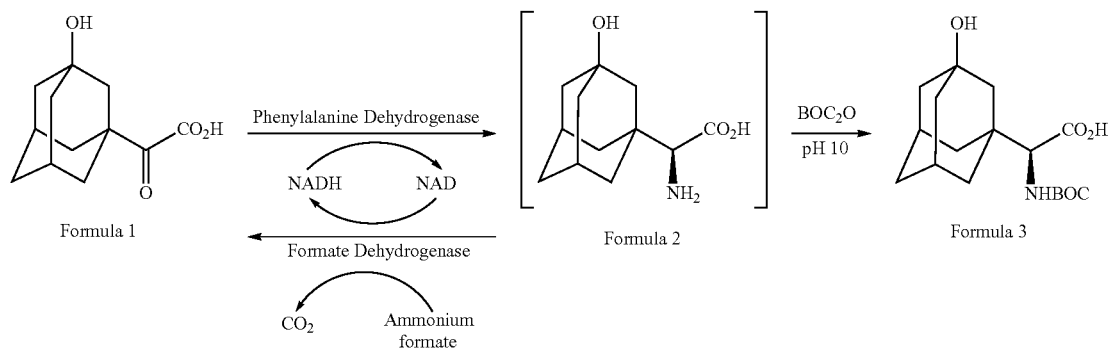

As shown in Scheme I, this reaction requires ammonia and reduced nicotinamide adenine dinucleotide (NADH). Nicotinamide adenine dinucleotide (NAD) produced during the reaction is recycled to NADH by the oxidation of formate to carbon dioxide by formate dehydrogenase. The expected yield of (αS)-α-amino-3-hydroxytricyclo[3.3.1.1$^{3,7}$]decane-1-acetic acid (Formula 2) from this reaction is 80 to 100% and the expected enantiomeric excess is greater than 99%. Also see Examples 1 through 7 herein.

The intermediate compound 3-hydroxy-α-oxotricyclo[3.3.1.1$^{3,7}$]decane-1-acetic acid (Formula 1) can be produced in accordance with the method depicted in Scheme II:

SCHEME II

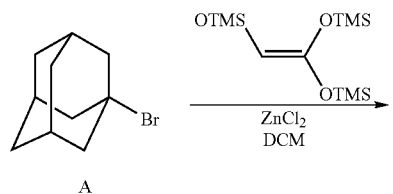

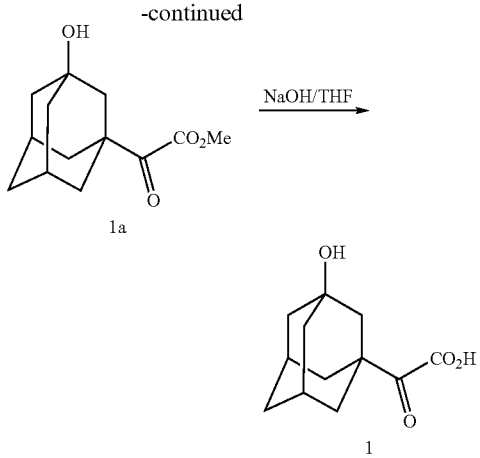

As shown in Scheme II, in this method, adamantyl bromide (Formula A) is alkylated via zinc chloride catalysis to produce α-hydroxytricyclo[3.3.1.1$^{3,7}$]decane-1-acetic acid (Formula B). α-Hydroxytricyclo[3.3.1.1$^{3,7}$]decane-1-acetic acid (Formula B) is then esterified using acetyl chloride in methanol to produce α-hydroxytricyclo[3.3.1.1$^{3,7}$]decane-1-acetic acid, methyl ester (Formula C). α-Hydroxytricyclo[3.3.1.1$^{3,7}$]decane-1-acetic acid, methyl ester (Formula C) is then converted to α-oxotricyclo[3.3.1.1$^{3,7}$]decane-1-acetic acid, methyl ester (Formula D) by Swern oxidation. α-Oxotricyclo [3.3.1.1$^{3,7}$]decane-1-acetic acid, methyl ester (Formula D) is then hydroxylated to form 3-hydroxy-α-oxotricyclo [3.3.1.1$^{3,7}$]decane-1-acetic acid, methyl ester (Formula 1a), which is then hydrolyzed to form 3-hydroxy-α-oxotricyclo [3.3.1.1$^{3,7}$]decane-1-acetic acid (Formula 1).

Alternatively, the intermediate compound 3-hydroxy-α-oxotricyclo [3.3.1.1$^{3,7}$]decane-1-acetic acid (Formula 1) can be produced in accordance with the method depicted in Scheme III.

SCHEME IIIA

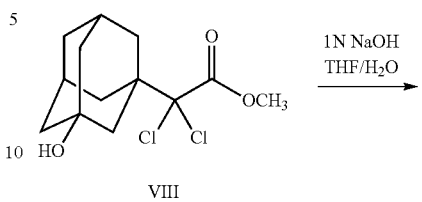

VIII

1N NaOH
THF/H$_2$O →

SCHEME III

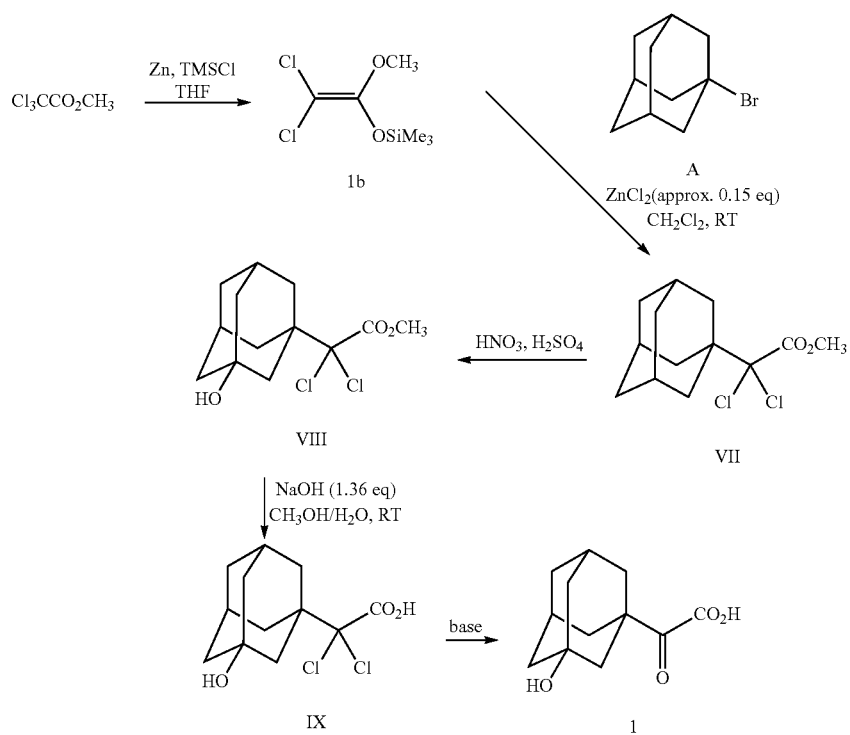

As shown in Scheme III, (2,2-dichloro-1-methoxy-vinyloxy)-trimethysilane 1b is prepared by minor modification of the method of Kuroda et al. (EP 08 08 824A3; Imashiro and Kuroda Tetrahedron Letters 2001 42:1313-1315). Treatment of bromoadamantane with 1b under the influence of zinc chloride (Reetz et al. Chem. Int. Ed. Engl. 1979 18:72, Reetz and Heimbach Chem. Ber. 1983 116:3702-3707, Reetz et al. Chem. Ber. 1983 116:3708-3724) yields adamantan-1-yl-dichloro-acetic acid methyl ester of Formula VII. Adamantan-1-yl-dichloro-acetic acid methyl ester of Formula VII is then hydroxylated with nitric oxide in concentrated sulfuric acid to provide a quantitative yield of dichloro-(3-hydroxy-adamantan-1-yl)-acetic acid methyl ester of Formula VIII. Hydrolysis of Formula VIII with aqueous sodium hydroxide in methanol at room temperature yields dichloro-(3-hydroxy-adamantan-1-yl)-acetic acid of Formula IX. Subsequent treatment of dichloro-(3-hydroxy-adamantan-1-yl)-acetic acid (Formula IX) with a weak base, preferably sodium bicarbonate, at elevated temperature results in the exclusive formation of the intermediate compound 3-hydroxy-α-oxotricyclo[3.3.1.1$^{3,7}$]decane-1-acetic acid (Formula 1).

-continued

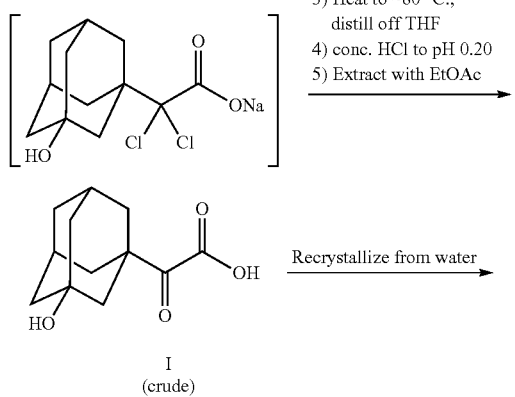

1) ~6N HCl to pH 7.4
2) NaHCO$_3$ (2.6 eq)
3) Heat to ~80° C., distill off THF
4) conc. HCl to pH 0.20
5) Extract with EtOAc →

Recrystallize from water →

I
(crude)

-continued

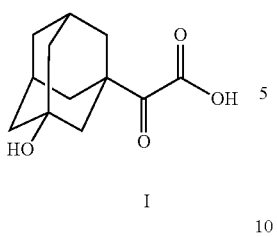

I

As shown in Scheme 111A, the intermediate compound 3-hydroxy-<a-oxotricyclo-[3.3.1.1³,⁷]decane-1-acetic acid (Formula I) may be prepared in a one pot procedure. As seen, treatment of Formula VIII compound with aqueous sodium hydroxide in tetrahydrofuran (or other base such as potassium hydroxide or lithium hydroxide) in an inert atmosphere such as argon, yields the corresponding sodium salt. Without recovering the sodium salt, the reaction mixture containing the sodium salt is treated with an acid such as hydrochloric acid to lower pH to less than about 0.50 preferably about 0.20, to form the corresponding keto acid II, which may be recrystallized from water to form crystals of the keto acid I.

The fragment (1S,3S,5S)-2-azabicyclo[3.1.0]hexane-3-carboxamide (Formula J) used in the production of (1S,3S,5S)-2-[(2S)-2-amino-2-(3-hydroxytricyclo[3.3.1.1³,⁷]dec-1-yl)-1-oxoethyl]-2-azabicyclo[3.1.0]hexane-3-carbonitrile can be produced in accordance with the method depicted in Scheme IV shown below.

SCHEME IV

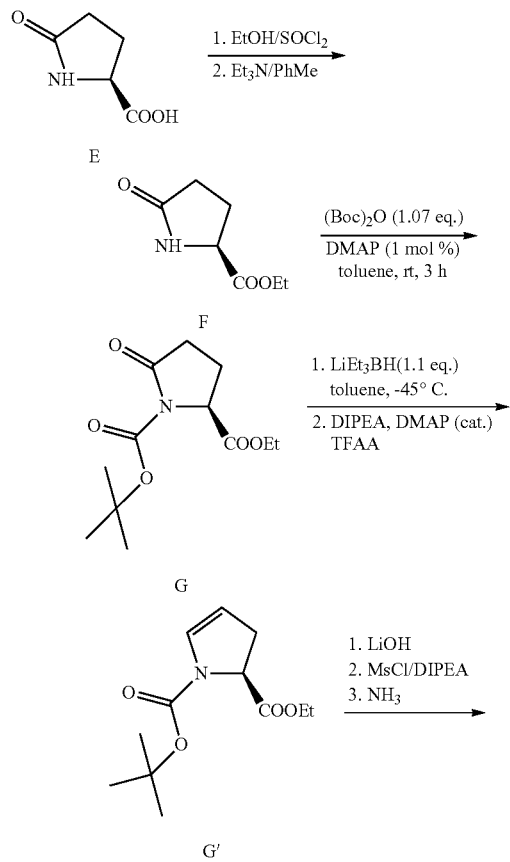

-continued

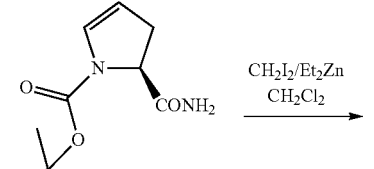

G''

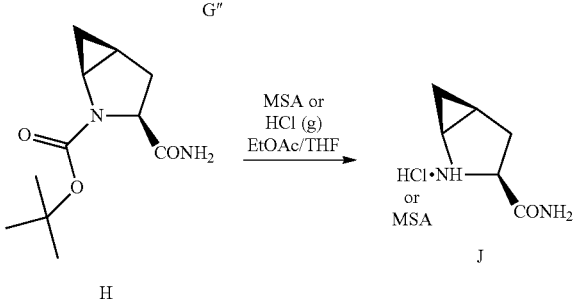

H

As shown in Scheme IV, L-pyroglutamic acid (Formula E) is first esterified to produce the L-pyroglutamic acid ethyl ester (Formula F; SQ 7539). This L-pyroglutamic acid ethyl ester is then BOC-protected on the nitrogen to produce (5S)-2-oxopyrrolidine-1,5-dicarboxylic acid, 1-(1,1-dimethylethyl),5-ethyl ester (Formula G). SuperHydride reduction and elimination is then performed to form 4,5-dihydro-1H-pyrrole-1,5-dicarboxylic acid, 1-(1,1-dimethylethyl),5-ethyl ester (Formula G'). The BOC-DHPEE III is then hydrolyzed by saponification with lithium hydroxide to form BOC-DHP. An amide is then formed on BOC-DHP via mixed anhydride using mesyl chloride followed by ammonia to produce (5S)-5-aminocarbonyl-4,5-dihydro-1H-pyrrole-1-carboxylic acid, 1-(1,1-dimethylethyl)ester (Formula G''). (5S)-5-aminocarbonyl-4,5-dihydro-1H-pyrrole-1-carboxylic acid, 1-(1,1-dimethylethyl)ester (Formula G'') is then cyclopropanated via the Simmons-Smith reaction to produce [1S-(1α,3β,5α]-3-aminocarbonyl)-2-azabicyclo[3.1.0]hexane-2-carboxylic acid, 1,1-dimethylethyl ester (Formula H). BOC is then removed resulting in formation of an acid salt such as the hydrochloride salt or the methanesulfonic acid salt of the fragment (1S,3S,5S)-2-azabicyclo[3.1.0]hexane-3-carboxamide (Formula J).

As seen in Scheme IV, the transformation of (5S)-5-aminocarbonyl-4,5-dihydro-1H-pyrrole-1-carboxylic acid, 1-(1,1-dimethylethyl)ester (Formula G'') to [1S-(1α,3β,5α]-3-aminocarbonyl)-2-azabicyclo[3.1.0]hexane-2-carboxylic acid, 1,1-dimethylethyl ester (Formula H) is effected by cyclopropanation in a Simmons-Smith Reaction. In this reaction, (5S)-5-aminocarbonyl-4,5-dihydro-1H-pyrrole-1-carboxylic acid, 1-(1,1-dimethylethyl)ester is dissolved in methylene chloride in a first reactor. In a second reactor, methylene chloride is cooled to −30° C. and dimethoxy ethane and a 30% solution of diethyl zinc in toluene are added followed by addition of diiodo methane. This mixture is then added to the first reactor followed by addition of saturated bicarbonate solution. The resulting reaction mixture is stirred until a precipitate formed. The precipitate is then filtered, washed and resuspended in methylene chloride two or more times. Filtrates are then separated into aqueous and organic phases and the organic phase is washed with half saturated brine. Solvent is removed and exchanged by heptane to obtain a slurry of crude product of [1S-(1α,3β,5α]-3-aminocarbonyl)-2-azabicyclo[3.1.0]hexane-2-carboxylic acid, 1,1-dimethylethyl ester (Formula H) in heptane.

Alternatively, (5S)-5-aminocarbonyl-4,5-dihydro-1H-pyrrole-1-carboxylic acid, 1-(1,1-dimethylethyl)ester (Formula G″) may be prepared as shown in Scheme IVA.

SCHEME IVA

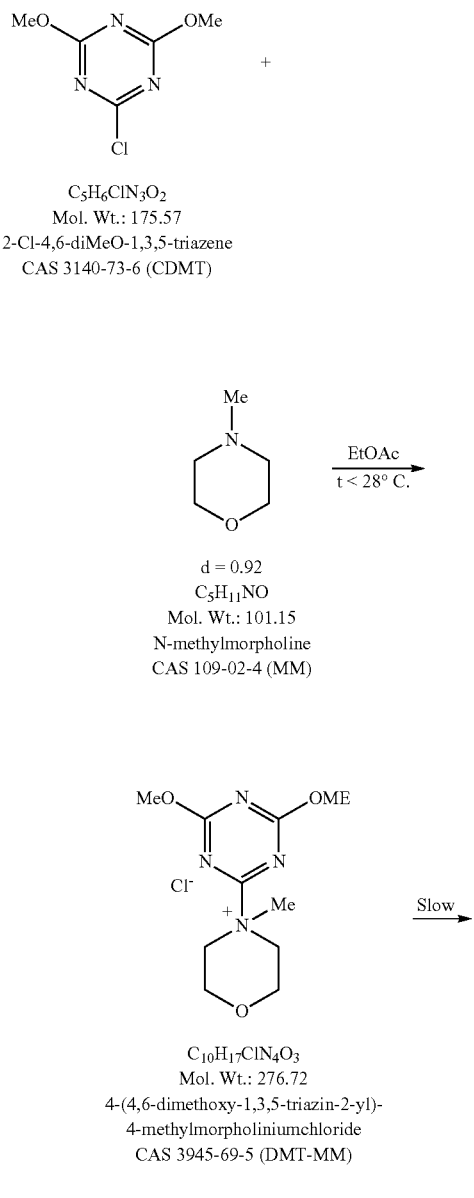

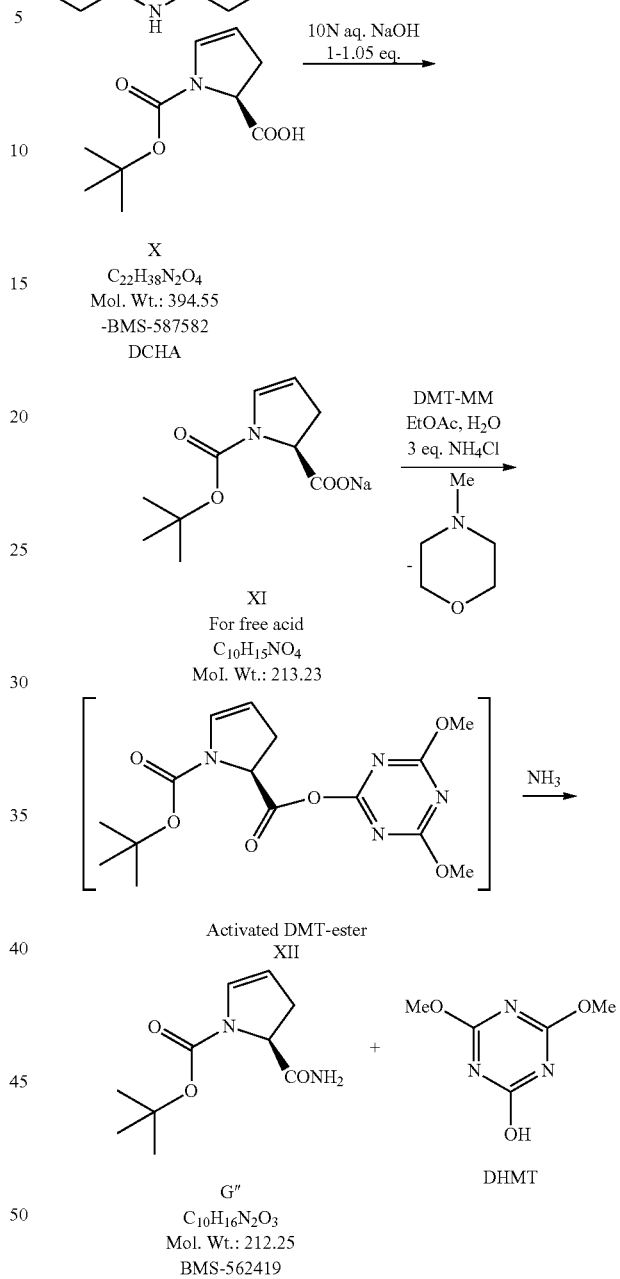

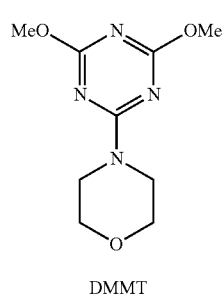

As shown in Scheme IVA, the DCHA salt of 4,5-dihydro-1H-pyrrole-1,5-dicarboxylic acid, 1-(1,1-dimethylethyl)ester X is treated with alkali metal base such as sodium hydroxide to form the corresponding salt, such as the sodium salt.

The sodium salt of 4,5-dihydro-1H-pyrrole-1,5-dicarboxylic acid, 1-(1,1-dimethylethyl)ester XI may also be prepared from the corresponding ethyl ester by treating the ethyl ester (preferably a solution of the ethyl ester in toluene) with ethanol and sodium hydroxide.

A solution of the sodium salt XI is treated with buffer such as ammonium chloride and sodium dihydrogen phosphate to lower pH of the solution below 7, preferably about 6 to 6.5, and the buffered solution of sodium salt is treated with 4-(4, 6-dimethoxy-1,3,5-triazin-2-yl)-4-methylmorpholinium chloride (DMT-MM) to form the activated DMT-ester XII which is treated with ammonia or other base such as ammonium sulfate, ammonium chloride or ammonium hydroxide, to form (5S)-5-aminocarbonyl-4,5-dihydro-1H-pyrrole-1-carboxylic acid 1-(1,1-dimethylethyl)ester G".

4-(4,6-Dimethoxy-1,3,5-triazin-2-yl)-4-methyl-morpholinium chloride (DTM-MM) may be prepared as shown in Scheme VIA by reacting 2-Cl-4,6-dimethoxy-1,3,5-triazine (CDMT) and N-methylmorpholine at reduced temperatures ranging from about 0 to about 10° C. to form DMT-MM.

The DCHA salt of 4,5-dihydro-1H-pyrrole-1,5-dicarboxylic acid, 1-(1,1-dimethylethyl)ester X may be prepared from the corresponding sodium salt XI by treating an aqueous solution of previously prepared DCHA salt X with methyl t-butyl ether (MTBE) adjusting pH of the reaction mixture to 2.5-3 employing an acid such as $H_3PO_4$. The organic layer is separated and treated with brine to form the corresponding sodium salt XI. The resulting reaction mixture is cooled and treated with DCHA to form the corresponding DCHA salt X.

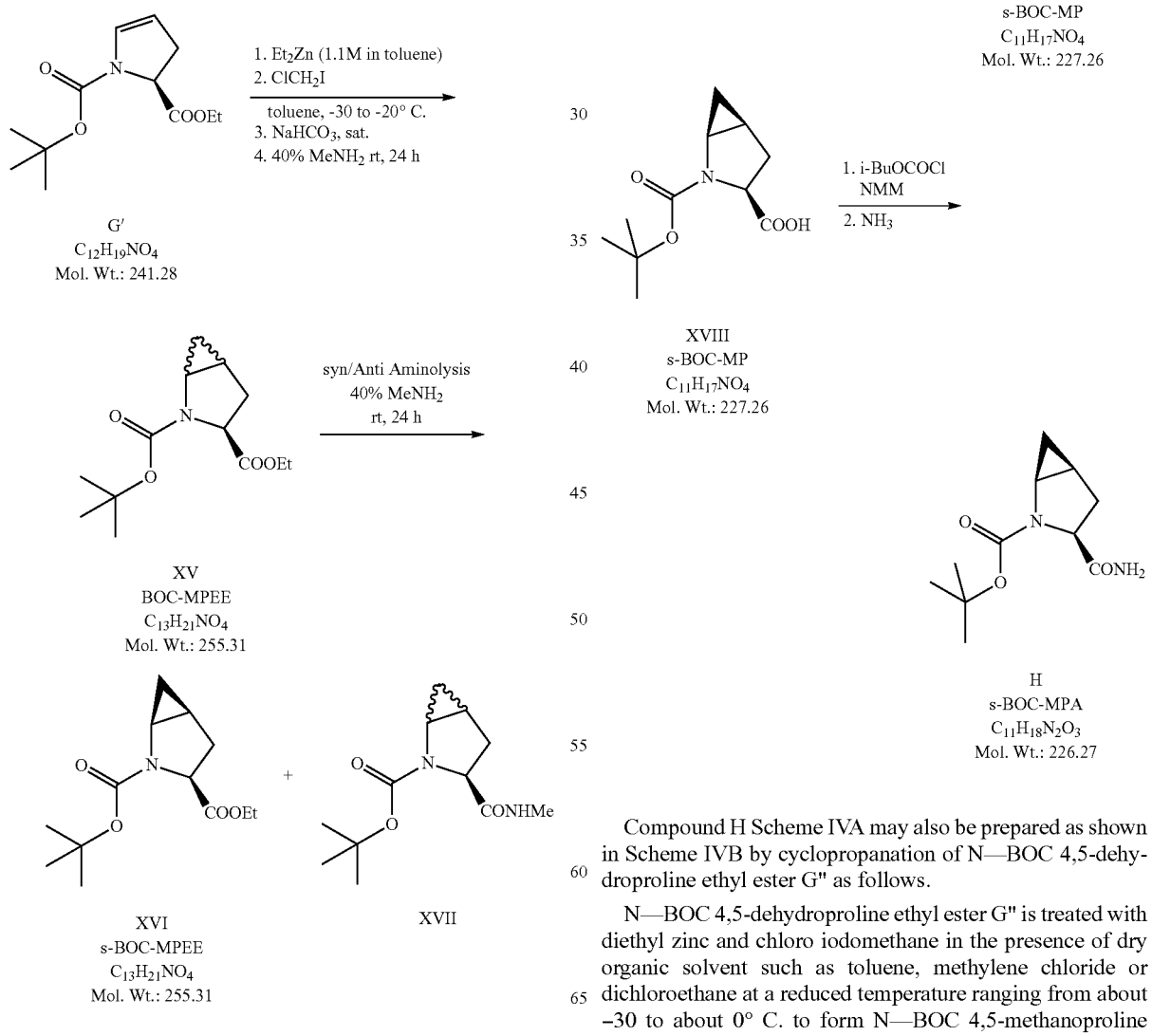

SCHEME IVB

Compound H Scheme IVA may also be prepared as shown in Scheme IVB by cyclopropanation of N—BOC 4,5-dehydroproline ethyl ester G" as follows.

N—BOC 4,5-dehydroproline ethyl ester G" is treated with diethyl zinc and chloro iodomethane in the presence of dry organic solvent such as toluene, methylene chloride or dichloroethane at a reduced temperature ranging from about −30 to about 0° C. to form N—BOC 4,5-methanoproline ethyl ester XV.

The resulting BOC 4,5-methanoproline ethyl ester XV (mixture of syn- and anti-isomers (8:1)) is separated by treating with aqueous methyl amine under an inert atmosphere such as a nitrogen atmosphere and syn (S)—BOC-4,5-methaneproline ethyl ester XVI (separated from XVII) is recovered.

The s-BOC-4,5-methanoproline ethyl ester XVI in ethanol or other organic solvent such as toluene or THF is treated with base such as aqueous lithium hydroxide, sodium hydroxide or potassium hydroxide to form the corresponding s-BOC-methanoproline free acid XVIII.

The free acid XVIII is converted to the corresponding s-BOC-methanoproline amide H by treating free acid XVIII dissolved in an organic solvent such as THF or methylene chloride; isobutyl chloroformate or mesyl chloride, in the presence of N-methyl morpholine, under reduced temperatures such as not to exceed about −8° C., and then treating the reaction mixture with ammonia to form the s-BOC-methanoproline amide H.

Another aspect of the present invention relates to a method for coupling the fragments (αS)-α-amino-3-hydroxytricyclo[3.3.1.1$^{3,7}$]decane-1-acetic acid (Formula 3) and (1S,3S,5S)-2-azabicyclo[3.1.0]hexane-3-carboxamide (Formula J) to produce (1S,3S,5S)-2-[(2S)-2-amino-2-(3-hydroxytricyclo[3.3.1.1$^{3,7}$]]dec-1-yl)-1-oxoethyl]-2-azabicyclo[3.1.0]hexane-3-carbonitrile, benzoate (1:1). Coupling of these fragments is depicted in Scheme V below.

SCHEME V

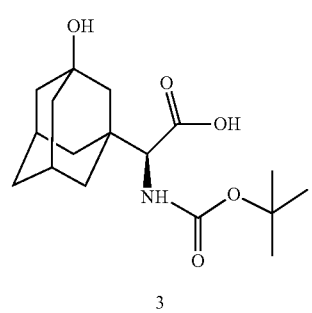

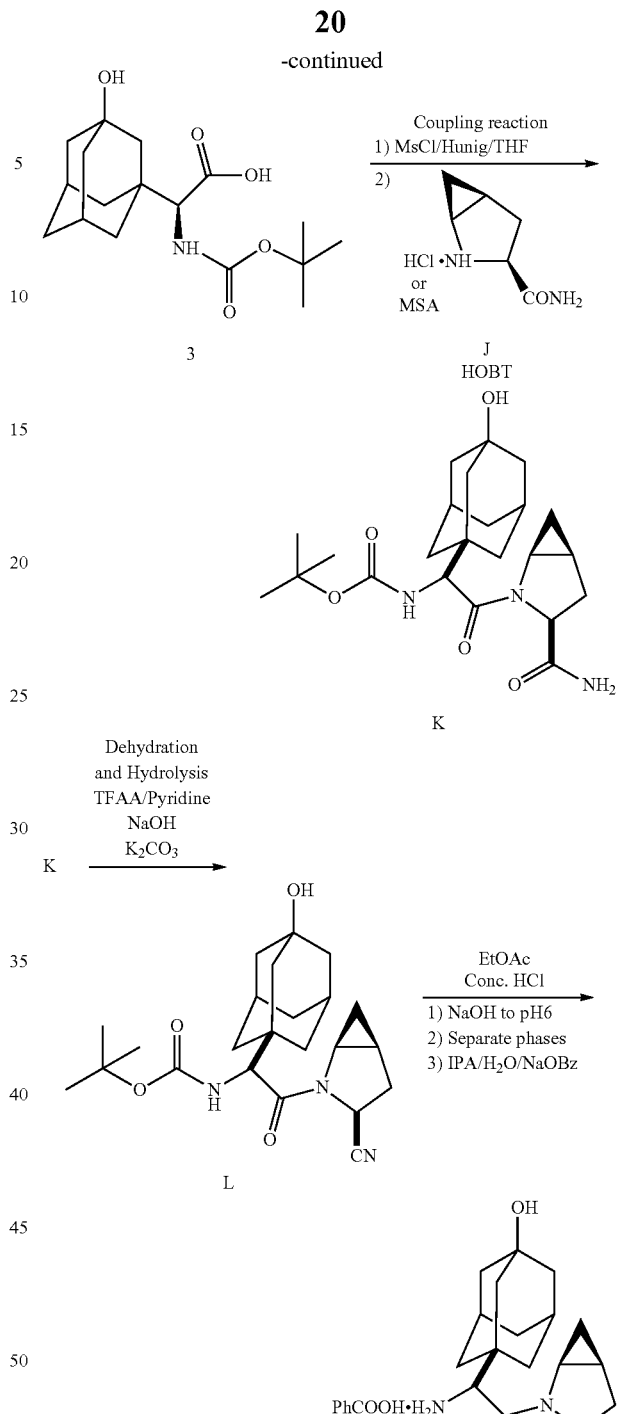

The compound of Formula 2 is used without isolation from a bioconversion using an isolated (partially purified) PDH/FDH enzyme concentrate as set out in the Example 3.

As shown in Scheme V, the fragment (αS)-α-amino-3-hydroxytricyclo[3.3.1.1$^{3,7}$]decane-1-acetic acid (Formula 2) is first BOC protected to produce (αS)-α[[(1,1-dimethylethoxy)carbonyl]amino]-3-hydroxytricyclo[3.3.1.1$^{3,7}$]decane-1-acetic acid (Formula 3) by treating 2 with BOC$_2$O in the presence of base such as sodium hydroxide and separated via isopropyl acetate extraction then crystallized with isopropyl acetate/heptanes to isolate the free acid 3 (see Example 3, step 3). Alternatively free acid 3 is separated via ethyl acetate (EtOAc) extraction (see Example 8M).

A solution of Formula 3 compound in an appropriate organic solvent such as tetrahydrofuran (THF) (cooled to a temperature within the range from about −10 to about 0° C.) is treated with methanesulfonyl chloride (Mesyl Cl), and Hunig base (diisopropylethylamine or DIPEA) to form the corresponding methanesulfonic acid salt of VI.

A coupling reaction is then used to couple (αS)-α[[(1,1-dimethylethoxy)carbonyl]amino]-3-hydroxytricyclo[3.3.1.1$^{3,7}$]decane-1-acetic acid, (Formula 3) methanesulfonic acid salt to (1S,3S,5S)-2-azabicyclo[3.1.0]hexane-3-carboxamide (Formula J) in the presence of 1-hydroxybenzotriazole (HOBT) or other known coupling agent to produce 3-(aminocarbonyl)-αS)-α-(3-hydroxytricyclo[3.3.1.1$^{3,7}$]dec-1-yl)-β-oxo-(1S,3S,5S)-2-azabicyclo[3.1.0]hexane-2-ethanecarbamic acid, 1,1-dimethylethyl ester (Formula K). Formula K compound is subjected to dehydration by treating compound K with organic base such as pyridine or triethylamine and trifluoroacetic anhydride, and then subjecting the reaction to hydrolysis by cooling to from about 0 to about 10° C. and adding sodium hydroxide or other strong base such as KOH or LiOH to form Compound L. 3-cyano-(αS)-α-(3-hydroxytricyclo[3.3.1.1$^{3,7}$]dec-1-yl)-β-oxo-(1S,3S,5S)-2-azabicyclo[3.1.0]hexane-2-ethanecarbamic acid, 1,1-dimethylethyl ester (Formula L), which is then deprotected (and treated with sodium benzoate) to form the dipeptidyl peptidase IV inhibitor (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) (Formula M).

Referring back to Scheme V, compound L may be deprotected by treatment with strong acid such as hydrochloric acid as described with respect to Scheme VIA.

SCHEME VIA

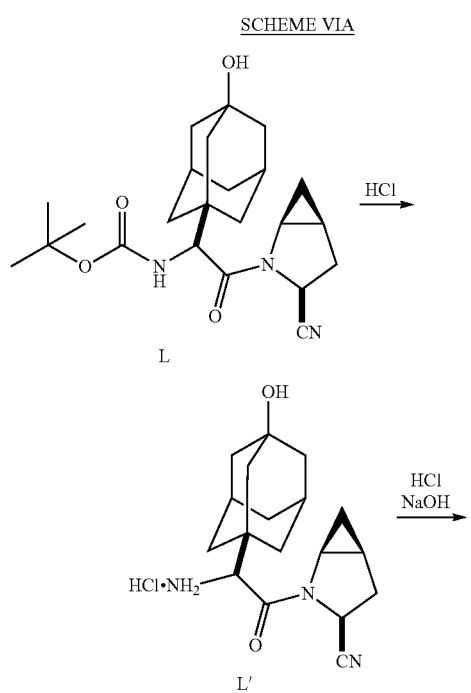

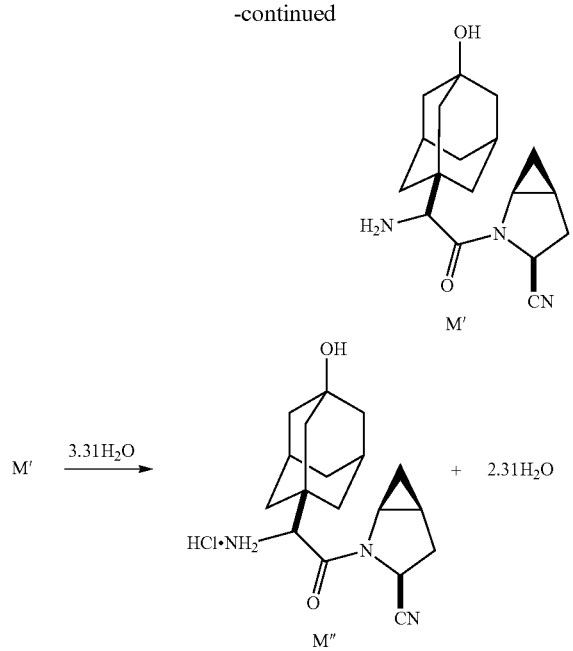

Referring to Scheme VIA, the free base monohydrate M″ may be formed from the BOC-protected intermediate L as follows.

BOC-protected intermediate L is treated with concentrated hydrochloric acid in the presence of methylene chloride and methanol while maintaining reaction temperature within the range from about 20 and 25° C., to form hydrochloride salt L′. Hydrochloride salt L′ is treated with hydrochloric acid and then sodium hydroxide or other strong base to form the free base M′. Free base M′ is then treated with water to form the free base monohydrate M″.

Dipeptidyl peptidase IV inhibition produced using the compounds and methods of the present invention are useful in the treatment of diabetes and complications thereof, hyperglycemia, Syndrome X, hyperinsulinemia, obesity, and atherosclerosis and related diseases as well as immunomodulatory diseases and chronic inflammatory bowel disease.

The following Examples represent preferred embodiments of the invention.

Example 1

Construction of Plasmid pBMS2000-PPFDH-PDHmod

A two-step construction of the expression vector pBMS2000-PPFDH-PDHmod was employed. The *P. pastoris* FDH gene was subcloned into expression vector pBMS2000 (pBMS2000 is disclosed in U.S. Pat. No. 6,068,991, issued May 30, 2000 to S. W. Liu et al.) using oligonucleotide primers containing the 5′ and 3′ end of the *P. pastoris* FDH gene along with compatible restriction endonuclease cleavage sites:

```
                            (5' end; sense; SEQ ID NO: 1)
     5' TCGTCATGAAAATCGTTCTCGTTTTG 3'
        BspHI (3' end; anti-sense; SEQ ID NO: 2)
     5' TACTGTTTTTCCAGCGTATTCCTAGGCT 3'
                              BamHI
```

High-fidelity PCR amplification of the *P. pastoris* FDH gene was carried out in four 100 µl aliquots, each containing 1× TaqPlus reaction buffer (Stratagene, LaJolla, Calif.), 0.2 mM each deoxynucleotide triphosphate (dATP, dCTP, dGTP, and dTTP), 0.4 nM each oligonucleotide, 2.5 U TaqPlus DNA polymerase (Stratagene), and 10 pg plasmid DNA containing the cloned *P. pastoris* FDH gene. The amplification conditions included incubation at 94° C. for 4 minutes, followed by 25 cycles of incubation at 94° C. for 1 minute; 50° C. for 1 minute; and 72° C. for 1.5 minutes, using a Perkin-Elmer Model 480 thermocycler with autoextension.

The PCR reaction mixture was extracted with an equal volume of 1:1 phenol:chloroform (GibcoBRL, Gaithersburg, Md.), and centrifuged at 13,000×g for 5 minutes. The upper aqueous phase was removed and placed in a new microcentrifuge tube. DNA was precipitated by addition of 0.1 volumes 3 M sodium acetate and 2 volumes ice-cold ethanol. After centrifugation at 13,000×g for 5 minutes, liquid was aspirated from the tube, and the pellet washed with 0.5 ml ice-cold 70% ethanol. Liquid was aspirated again, and the pellet was allowed to air dry for 30 minutes at room temperature.

Amplified DNA was digested with 20 units each of BspHI and BamHI for 3 hours at 37° C. in a total volume of 50 µl. In parallel, the pBMS2000 vector (2 µg) was digested with BspHI and BamHI. The digested samples were electrophoresed on a 1.0% TAE agarose gel for 2 hours at 100 v. The bands corresponding to the FDH gene (1100-base pair fragment) and linearized vector (4700-base pair fragment) which were separately excised from the gel and purified using the QIAquick Gel Extraction Kit (Qiagen, Chatsworth, Calif.). The concentrations of the isolated fragments were estimated by electrophoresis against the low molecular weight mass ladder (Invitrogen Corp., Carlsbad, Calif.) and ligated in a 5:1 (insert:vector) molar ratio in a total volume of 10 µl at 22° C. for 2 hours. DNA was precipitated by addition of 15 µl dH$_2$O and 250 µl 1-butanol, and pelleted at 13,000×g in a microcentrifuge for 5 minutes. Liquid was removed by aspiration, and the DNA was dried in a SpeedVac (Savant Instruments, Farmingdale, N.Y.) for 5 minutes under low heat. The pellet was resuspended in 5 µl dH$_2$O.

The resuspended DNA was transformed by electroporation into 0.04 ml *E. coli* DH10B competent cells (Invitrogen) at 25 µF and 250Ω. SOC medium was immediately added (0.96 ml; SOC=0.5% yeast extract, 2% tryptone, 10 mM NaCl, 2.5 mM KCl, 10 mM MgCl$_2$, 10 mM MgSO$_4$, and 20 mM glucose per liter), and the cells incubated in a shaker for 1 hour at 37° C. and 225 rpm. Colonies contain plasmid DNA were selected on LB agar plates containing 50 µg/ml kanamycin sulfate (Sigma Chemicals, St. Louis, Mo.). Plasmids with the desired insert were identified by colony PCR in capillary tubes using the RapidCycler (Idaho Technology, Salt Lake City, Utah). Each reaction mixture contained 50 mM Tris-HCl (pH 8.3), 4 mM MgCl$_2$, 0.25 mg/ml bovine serum albumin, 2% sucrose 400, 0.1 mM cresol red, 0.4 nM each primer (SEQ ID NO:1 and SEQ ID NO:2), and 2.5 U Taq DNA polymerase (Promega Corp., Madison, Wis.). The reaction mixture was divided into 10 µl aliquots, and pipetted into the wells of a round-bottom microtiter plate. A kanamycin-resistant colony was picked using a disposable plastic inoculation needle, swirled into the reaction mixture, and transferred to LB-kanamycin agar. Each reaction mixture aliquot was drawn into a 30 µl capillary tube, and the tube was flame-sealed at both ends. Cells were lysed and DNA denatured by incubation at 94° C. for 30 seconds; amplification was performed using 30 cycles of incubation at 94° C. for 0 seconds; 40° C. for 0 seconds, and 72° C. for 60 seconds using a RapidCycler Thermocycler (Idaho Technologies, Salt Lake City, Utah). Samples were electrophoresed on a 1.0% TAE agarose gel for 2 hours at 100 v. Seven samples out of 17 tested showed a strong band at 1100 base pairs. One colony containing this plasmid (referred to herein as pBMS2000-PPFDH) was chosen for the next step in the plasmid construction.

"PDHmod" refers to a modified *Thermoactinomycetes intermedius* phenylalanine dehydrogenase that differs from the published DNA sequence (Takada et al., J. Biochem. 109, pp. 371-376 [1991]) by a change of the last two amino acids and an additional 12 amino acids at the carboxyl terminus that is required for complete conversion of (3-hydroxy-adamantan-1-yl)-oxo-acetic acid to (S)-amino-(3-hydroxy-adamantan-1-yl)-acetic acid. This change was introduced into plasmid pPDH9K/10 (described in detail by in patent WO 200004179, issued to Donovan et al., Jan. 27, 2000), which was subsequently transformed into *P. pastoris* SMD1168 (deposited as strain ATCC 74408).

3' end of native PDH gene and corresponding amino acids:

```
AAC AGC GCA AGG AGG TAA
Asn Ser Ala Arg Arg Stop
```

3' end of PDHmod gene and corresponding amino acids (changed or new amino acids in bold):

```
AAC AGC GCG GAG GGG TAC CTC GAG CCG CGG
Asn Ser Ala Glu Gly Tyr Leu Glu Pro Arg

CGG CCG CGA ATT AAT TCG CCT TAG
Arg Pro Arg Ile Asn Ser Pro Stop
```

Oligonucleotide primers containing the 5' and 3' end of the PDHmod gene along with compatable restriction endonuclease cleavage sites were prepared:

```
                     (5' end, sense; SEQ ID NO: 3)
GATGCTCATATGCGCGACGTGTTTGAAATGATG
      NdeI (3' end, anti-sense; SEQ ID NO: 4)
GATCCCGGGCTAAGGCGAATTAATAATTCG
   SmaI
```

Reaction conditions for amplification and purification of the PDHmod by PCR were identical to that used for the *P. pastoris* FDH gene except chromosomal DNA prepared from ATCC 74408 was included as template for the reaction. The resulting fragment was digested with 20 units each of NdeI and SmaI for 1 hour at 25° C., followed by 2 hours at 37° C., in a total volume of 50 µl. In parallel, a version of the pBMS2000 vector with an NdeI site at the initiation codon (2 µg) was digested with NdeI and SmaI using identical conditions. The digested samples were separately electrophoresed on a 1.0% TAE agarose gel for 2 hours at 100 v. The bands corresponding to the PDHmod gene (1200-base pair fragment) and linearized vector (4700-base pair fragment) were excised from the gel and purified using the QIAquick Gel Extraction Kit (Qiagen). Ligation of the two fragments, transformation of *E. coli*, and screening for colonies containing inserts with the PDHmod gene (forming pBMS2000-PDHmod) were performed as described supra.

For construction of pBMS2000-PPFDH-PDHmod, pBMS2000-PDHmod (2 µg) was cleaved with 10 U each HindIII and SmaI in a 50 µL reaction for 1 hour at 25° C., followed by 1 hour at 37° C. Ten units of T4 DNA polymerase (Invitrogen) and 2 µL of a 2.5 mM mixture of all four deoxyribonucleoside triphosphates were added and the sample incubated at 11° C. for 20 minutes. The reaction was electrophoresed on a 1.0% TAE agarose gel for 2 hours at 100 v. The 1800-base pair fragment was excised and isolated using the QIAquick Gel Extraction Kit (Qiagen). This fragment contains, in order, the tac promoter, groES gene, and the PDHmod gene (as a transcriptional fusion). Next, pBMS2000-PPFDH (2 µg) was digested with 10 units restriction endonuclease SmaI in a 50 µL volume for 2 hours at 25° C., then treated with 0.4 U shrimp alkaline phosphatase (United States Biochemicals, Cleveland, Ohio) for 1 hour at 37° C. Plasmid DNA was electrophoresed for 2 hours at 100 v on a 1.0% TAE agarose gel, isolated, and extracted with the QIAquick kit. The two fragments were ligated in a 6.5:1 (insert:vector) molar ratio at 16° C. for 4 hours in a 10 µL final volume. After 1-butanol extraction and centrifugation, the DNA was transformed into electrocompetent DH10B cells. Kanamycin-resistant colonies were screened for the presence of the PDHmod gene with the two PDHmod-specific primers as previously described for FDH. A second round of PCR screening was conducted by using DNA primers homologous to the 5' end of the PPFDH and 3' end of the PDHmod gene, respectively. Only those constructs able to support amplification of a 1400-base pair fragment possessed the two genes in the same orientation. One such plasmid was found and the orientation confirmed by diagnostic restriction digestion with KpnI, which gave the expected fragments of 5422 and 1826 base pairs. This plasmid was designated "pBMS2000-PPFDH-PDHmod."

Example 2

Expression of FDH and PDHmod pBMS2000-PPFDH-PDHmod was transformed into *Escherichia coli* JM110. In shake-flasks studies, JM110 (pBMS2000-PPFDH-PDHmod) was grown for 18 hours at 28° C., 250 rpm in MT5 medium (2.0% Yeastamine, 4.0% glycerol, 0.6% sodium phosphate [dibasic], 0.3% potassium phosphate [monobasic], 0.125% ammonium sulfate, 0.0256% magnesium sulfate [heptahydrate; added post-autoclaving from a sterile 1 M solution], and 50 µg/ml kanamycin sulfate [added post-autoclaving from a filter-sterilized 50 mg/ml solution]). The optical density at 600 nm ($OD_{600}$) was recorded and cells sufficient to give a starting $OD_{600}$ of 0.35 were added to fresh MT5/kanamycin medium. Flasks were shaken at 250 rpm, 28° C. until the $OD_{600}$ was 0.8-1.0. Expression of both genes was induced by addition of filter-sterilized 1M isopropylthio-β-D galactopyranoside (IPTG) to a final concentration of 35 µM and the fermentation continued for 24-48 hours. Cells were pelleted by centrifugation at 6,500×g for 5 minutes, washed once with an equal volume of 50 mM ammonium formate pH 7.0, and repelleted. Cells were stored frozen at −20° C. or used immediately. The pellet was resuspended in 50 mM ammonium phosphate, pH 7.0 at 10 mL/g wet cell weight and sonicated 3×15 seconds using a Fisher Scientific Model 50 Sonic Dismembrator (Fisher Scientific, Pittsburgh, Pa.), power setting 15 with a microtip. Debris was pelleted by centrifugation at 13,000×g for 5 minutes at room temperature.

Expression was examined by sodium dodecyl sulfate-polyacrylamide gel electrophoresis (SDS-PAGE). One µL of the cell extract was mixed with 5 µL of 4× NuPAGE™ LDS buffer (Invitrogen) and brought up to 19 mL with distilled water. Samples were heated at 70° C. for 10 minutes. One mL of a 1M dithiothreitol solution was added to the mixture and 10 µL applied to a 10% NuPAGE™ Bis-Tris polyacrylamide mini-gel. Electrophoresis was carried out at 200 v for 50-60 minutes and the gel stained in a solution consisting of 0.1% (w/v) Coomassie Blue (Sigma), 40% (v/v) ethanol, and 10% (v/v) acetic acid. The gel, immersed in the stain, was heated in a microwave oven until boiling was evident, then shaken at 40 rpm on an orbital shaker for 15 minutes. The gel was washed thoroughly with deionized water and covered with destaining solution (GelClear™; Invitrogen). The solution was again heated just to the point of boiling and shaken gently for at least 2 hours. Two prominent bands at $M_r$ 43,000 and 40,000 were seen upon induction, corresponding to the expected molecular weight of the subunits of FDH and PDHmod. Samples were also found to possess both FDH and PDH activities when tested as described in Examples 4, 6 and 7. This recombinant *E. coli* strain was given the internal designation of SC 16496.

SC 16496 was subsequently fermented at 15- and 250-liter volumes. For a 15-liter fermentation, one vial containing 1 mL of frozen SC 16496 was thawed at room temperature and added to 1 liter of MT5 medium containing 50 µg/ml kanamycin in a 4-liter flask. The flask was incubated at 28° C., 250 rpm for 24 hours and transferred to 13 liters of MT5 medium (ingredients batched based on a final volume of 15 L) in a Braun fermentor. Kanamycin sulfate and magnesium sulfate heptahydrate sufficient to give a final concentration of 50 µg/ml and 0.0246%, respectively, were dissolved in 500 mL distilled water and filter-sterilized through a 0.2 micron cellulose acetate filtration unit. The solution was added to the tank, followed immediately by the inoculum. The initial $OD_{600}$ was ca. 0.35.

Fermentation operating parameters were as follows:

16 liter working volume

Temperature: 28° C.

Aeration: 1.0 vvm

Pressure: 690 mbar

Agitation: 500 rpm

Control pH at 6.8 with $NH_4OH$ as required

Foaming was controlled by addition of UCON (a fluorocarbon solvent blend produced by Dow Chemical Company) on demand.

At $OD_{600}$ 0.8-1.0 (approximately two hours after inoculation), filter-sterilized IPTG (dissolved in 500 mL $dH_2O$) was added aseptically to give a final concentration of 35 µM. The fermentation continued for an additional 48 hours, whereupon the contents of the tank were subcooled to 10° C. Cells were collected by centrifugation and rinsed once with 0.1 vol 50 mM ammonium formate pH 7.0. The cell paste was placed into plastic containers and stored at −70° C. until needed.

For 250-L tanks, the inoculum was prepared as follows: 1 mL of frozen SC 16496 was thawed and added to 300 mL MT5 medium with 50 µg/ml kanamycin. The flask was grown at 28° C., 250 rpm for 24 hours. The $OD_{600}$ was determined and the appropriate volume of cells to give 80 OD units was removed and added to 250 mL fresh MT5 medium. The cells were aseptically added to 10 L of MT5/kanamycin medium in a Braun fermentor (initial $OD_{600}$~0.008) and grown under the Fermentation Operating Parameters disclosed supra for 16 hours. The culture was then transferred to 250 L of MT5 containing the appropriate concentrations of kanamycin and magnesium sulfate. Based on the 90 minute doubling time of SC 16496 under these conditions, 10 L of inoculum in 250 L should give a starting $OD_{600}$ of 0.30-0.35. Induction, growth, harvesting, and storage were carried out as described for the 15-L fermentation.

Example 3

Telescoped Production of (αS)-α-[[(1,1-dimethylethoxy)carbonyl]amino]-3-hydroxytricyclo[3.3.1.1$^{3,7}$]decane-1-acetic acid (Formula 3) from 3-hydroxy-α-oxotricyclo-[3.3.1.1$^{3,7}$]decane-1-acetic acid (Formula 1) through (αS)-α-amino-3-hydroxytricyclo[3.3.1.1$^{3,7}$]decane-1-acetic acid (Formula 2) using an isolated (partially purified) PDH/FDH enzyme concentrate Step 1: Isolation of PDH/FDH Enzyme Concentrate Fermentation broth (30 liters) of *Escherichia coli* JM110 (pBMS2000-PPFDH-PDHmod) was obtained from a 4000 L tank fermentation (prepared using the procedure similar to Example 2) and passed through a microfluidizer (Microfluidics model M-110Y, operating pressure 12,000-20,000 psi) (one pass) to release the activity from the cells keeping the temperature of the broth below 40°. The PDH/FDH activity of microfluidized broth was 32 IU/ML for PDH and 8 IU/ml for FDH.

To clarify the whole broth, 4.5 kg of Celite was added to well-stirred broth. Then 0.201 liters of 30% aq. polyethyleneimine was added and mixed for 30 minutes. The mixture was then filtered using a filter press (Ertel Alsop model 8-ESSC-10) and 18 liters of filtrate was obtained. The filter cake was washed with 12 liters of water to bring the volume back to 30 liters. The step yield was 97% activity recovery of PDH with an activity of 31 IU/ml and a FDH activity of 8 IU/ml.

The clarified broth was ultrafiltered through a 100,000 MWCO filter cassette (Millipore Pellicon 2 unit, polyethersulfone low protein binding cassette, 0.5 m$^2$ filter area). The circulation rate of the pump was 400 mL/min. The clarified filtrate was concentrated to 1.5 liters and gave an enzyme concentrate with PDH titer of 567 IU/ml and FDH titer of 136 IU/ml. The permeate was assayed and no activity was found. The overall enzyme activity recovery in the concentrate was 84%.

Step 2: Reductive Amination

3-Hydroxy-α-oxotricyclo-[3.3.1.1$^{3,7}$]decane-1-acetic acid (Formula 1) (1.00 kg; 4.46 mol) was added to a 20 L vessel followed by water (5 L). The mixture was stirred and the pH was adjusted to pH-8 with 10N NaOH to give a solution. Darco KBB carbon (100 g) was added and the mixture was stirred for 5 minutes then filtered through a Buchner funnel with 5μ filter paper. The filter was washed with water (2×μL) and the filtrates and washes were combined to give a clear solution.

With stirring, ammonium formate (0.562 Kg; 8.92 mol) was added and the pH was re-adjusted to ~7.5 with 10N NaOH. Nicotinamide adenine dinucleotide (2.65 g) and dithiothreitol (1.54 g) were added. When the solids had dissolved, a PDH/FDH enzyme concentrate was added (1.03 L; 500,000 IU of PDH). The pH was re-adjusted to ~8.0 with 10N NaOH at ambient temperature.

The mixture was then warmed to ~40° C. and diluted to a total volume of 10 L with water. The pH was maintained at 7.7-8.3 while stirring over 42 hours. The resulting solution contained 0.955 Kg (95.1%) of the product (αS)-α-amino-3-hydroxytricyclo[3.3.1.1$^{3,7}$]decane-1-acetic acid (Formula 2).

Step 3: BOC-Protection

Di-tert-butyl dicarbonate (1.022 kg; 4.68 mol) was added to a portion of the solution of (αS)-α-amino-3-hydroxytricyclo[3.3.1.1$^{3,7}$]decane-1-acetic acid (Formula 2) (477.5 g; 2.12 mol). This mixture was stirred at ambient temperature, with pH adjusted to and maintained at 10 with a pH stat titrator using 10N NaOH. The reaction was complete 4 hrs after Boc$_2$O addition when there was less than 1.0% starting material remaining.

The pH of the mixture was adjusted to ~8 with 35% H$_2$SO$_4$ and i-PrOAc (5.0 L) was added to the mixture. The pH of the mixture was then adjusted to 2.0 with 35% H$_2$SO$_4$ and maintained at this pH for 5-10 min. Dicalite (250 g) was added; the mixture was stirred for ~10 min, and then filtered through a pad of Dicalite (250 g) on filter paper in a Buchner funnel. The Dicalite pad was further washed with 2.5 L i-PrOAc.

The filtrate was adjusted to pH 8 with 10N NaOH. After settling for 1 hr, the organic layer including interface was discarded. To the aqueous layer, i-PrOAc (7.5 L) was added. The mixture was acidified with 35% H$_2$SO$_4$ to pH~2, and then heated to and maintained at ~40° C. for 4 hours with mild stirring. The layers were separated and the organic extract was saved. The aqueous layer with interface was extracted with i-PrOAc (3.75 L) and the layers were again separated after 2 hrs at 40° C. The aqueous layer with interface was extracted again with i-PrOAc (3.75 L) and the layers were separated after 2 hrs at 40° C.

The combined organic extracts (~15 L) were concentrated by distillation to ~4.5 L. To this solution, heptane (~10 L) was then added over 10-15 min while the temperature was maintained at ~82-89° C. The reactor jacket temperature was set to 70° C. and maintained at this temperature for 1 hr. Crystallization occurred shortly after cooling. The reactor jacket temperature was then set at 40° C. and maintained at this temperature for 30 min.

The suspension was cooled down to ambient temperature, and then further cooled to 0-5° C. After one hour of stirring at 0-5° C., the product was filtered. The product was washed with heptane (2.5 L), then dried in vacuo at 40° C. to give 607.0 g (88% yield) of (αS)-α-[[(1,1-dimethylethoxy)carbonyl]amino]-3-hydroxytricyclo[3.3.1.1$^{3,7}$]decane-1-acetic acid (Formula 3).

Example 4

Phenylalanine Dehydrogenase Assay A

Phenylalanine dehydrogenase assay A contained in 1 ml at 40° C.: 0.4 mM NADH, 5 mM sodium phenylpyruvate, 0.75M NH$_4$OH adjusted to pH 8.75 with HCl. Absorbance decrease was monitored at 340 nm. Enzyme activity units were calculated as μmoles/minute based on the rates of absorbance change.

Example 5

Phenylalanine Dehydrogenase Assay B

Phenylalanine dehydrogenase assay B contained in 1 ml at 40° C.: 1 mM NAD, 10 mM L-phenylalanine, 0.1 M K$_2$HPO$_4$ adjusted to pH 10.0 with 1 N NaOH. Absorbance increase was monitored at 340 nm. Enzyme activity units were calculated as μmoles/minute based on the rates of absorbance change.

Example 6

Phenylalanine Dehydrogenase Assay C

Phenylalanine dehydrogenase assay C contained in 1.0 mL at 40° C.: 0.4 mM NADH, 50 mM 3-hydroxy-α-oxotricyclo[3.3.1.1$^{3,7}$]decane-1-acetic acid (dissolved in 1 equivalent NaOH solution), 0.75M NH$_4$OH adjusted to pH 8.75 with HCl. Absorbance decrease was monitored at 340 nm. Enzyme activity units were calculated as μmoles/minute based on the rates of absorbance change.

Example 7

Formate Dehydrogenase Assay

The formate dehydrogenase assay contained in 1.0 ml at 40° C.: 1 mM NAD, 100 mM ammonium formate, 100 mM potassium phosphate buffer, pH 8.0. Absorbance increase was monitored at 340 nm. Enzyme activity units were calculated as μmoles/minute based on the rates of absorbance change.

Example 8

Preparation of:

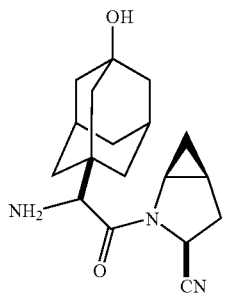

M'

A. $ZnCl_2$-Catalyzed Adamantyl Bromide (Formula A) Coupling

A dry vessel was charged with 7.5 kg adamantyl bromide. Methylene chloride (22.5 liters) was then added at room temperature to dissolve the solid adamantane bromide. Dissolving is endothermic so before the next step, the temperature of the reaction mixture was allowed to return to 20° C. The reaction mixture was then charged with zinc chloride (1.05 kg) and stirred for approximately 5 minutes at 20° C. The reaction mixture was then charged with tris(trimethylsiloxy)-ethylene (15.3 kg) while maintaining the reaction temperature between 20 to 25° C. and the resulting mixture was stirred for 2 hours. Following this mixing, tris(trimethylsiloxy)-ethylene (5.10 kg) was added. During this addition, the temperature was maintained below 30° C. The reaction was maintained for another 12 to 15 hours at 20 to 25° C., at which time the reaction mixture was diluted with methylene chloride (15 liters) and cooled to 0 to 5° C. The reaction mixture was then treated, beginning in dropwise fashion, with half-saturated $NH_4Cl$ solution. During addition, the temperature was kept below 30° C. A thick suspension was obtained. To this suspension was added ethyl acetate (93.75 liters). The mixture was stirred vigorously for 15 minutes and the organic and aqueous phases were split. The organic layer was stored and the aqueous layer was washed twice with ethyl acetate (18.75 liters in each wash). The ethyl acetate washes and organic layer were then combined and washed with water (37.5 liters) followed by water half saturated with brine (37.5 liters). The organic layer was separated again and evaporated to form crystals. A solvent exchange to heptane was then performed at a final volume of 22.5 liters. The resulting suspension was cooled to 5 to 10° C. for 1 hour and the product α-hydroxytricyclo[3.3.1.1$^{3,7}$]decane-1-acetic acid (Formula B) was obtained via filtration. Yield of α-hydroxytricyclo[3.3.1.1$^{3,7}$]decane-1-acetic acid (Formula B) was 6.96 kg (33.11 mol, 95%).

B. Esterification of α-hydroxytricyclo[3.3.1.1$^{3,7}$] decane-1-acetic acid (Formula B) to Form Ester of Formula C An inert atmosphere was first created in the reactor. The reactor was then charged with methanol (35.00 liters) followed by α-hydroxytricyclo[3.3.1.1$^{3,7}$]decane-1-acetic acid (Formula B) (14.00 kg) to form a suspension. The suspension was cooled to 0 to 5° C. and acetyl chloride was added in a manner such that the temperature of the reaction mixture was kept between 5 and 10° C. After completion of the addition of acetyl chloride, the reaction mixture was warmed to 20 to 25° C. and stirred for 2 hours at 20 to 25° C. The reaction mixture was than concentrated under vacuum at 40° C. and a thin oil was obtained. The oil was dissolved in ethyl acetate (71.96 liters) and brought to room temperature. The resulting mixture was washed twice in water (28.78 liters each wash) and the organic and aqueous layers were separated after each wash. The organic layer was stored while the aqueous layers were combined and adjusted to pH 9.5 with 3 N NaOH solution. The combined aqueous layers were then extracted twice with ethyl acetate (14.39 liters with each extraction). The organic layers following each extraction were separated and combined with the stored organic layer. These combined organic layers were then washed with saturated sodium bicarbonate solution (28.78 liters) followed by brine (43.18 liters). All volatiles were then removed under vacuum at 40° C. and a colorless to slightly yellow oil which crystallized on standing was obtained. This oil contained 13.29 kg (59.26 mol, 89%) α-hydroxytricyclo[3.3.1.1$^{3,7}$]decane-1-acetic acid, methyl ester (Formula C).

C. Swern Oxidation of α-hydroxytricyclo[3.3.1.1$^{3,7}$] decane-1-acetic acid, methyl ester (Formula C) to form α-oxotricyclo[3.3.1.1$^{3,7}$]decane-1-acetic acid, methyl ester (Formula D)

A three-necked flask (22 liters) was equipped with a mechanical stirrer, temperature probe and an addition funnel and purged with nitrogen overnight. Oxalyl chloride (500 ml, 5.73 mol) was then added followed by $CH_2Cl_2$ (8 liters). The resulting solution was cooled to −69° C. with an acetone/dry ice bath. A solution of dimethylsulfoxide (DMSO; 700 ml, 9.86 mol) was then slowly added over approximately 30 minutes while keeping the internal temperature below −60° C. The solution was stirred for 20 minutes while maintaining the temperature at −60 to −70° C. A solution of α-hydroxytricyclo[3.3.1.1$^{3,7}$]decane-1-acetic acid, methyl ester (Formula C) (990 grams, 4.42 mol) in $CH_2Cl_2$ (1.7 liters) was then slowly added over approximately 30 minutes while keeping the internal temperature below −60° C. The resulting solution was stirred for 30 minutes. $NEt_3$ (3 liters, 21.5 mol) was then added to form a heavy slurry of triethylamine hydrochloride salt. The reaction mixture was warmed to room temperature and water (1 liter) was added to dissolve triethyl ammonium salt (TEA salt). The reaction mixture was then transferred to a round bottom flask, and concentrated down to remove dichloromethane (DCM) and $NEt_3$. EtOAc (12 liters) was added and the resulting aqueous and organic layers were split. The organic layer was washed three times with water (2 liters each wash) followed by a brine wash (2 liters). The organic phase was then dried over anhydrous $Na_2SO_4$ with evaporation to produce a slight yellow solid of α-oxotricyclo[3.3.1.1$^{3,7}$]decane-1-acetic acid, methyl ester (Formula D). Yield was approximately 104%.

D. Hydroxylation of α-Oxotricyclo[3.3.1.1$^{3,7}$]decane-1-acetic acid, methyl ester (Formula D) to 3-hydroxy-α-oxotricyclo[3.3.1.1$^{3,7}$]decane-1-acetic acid, methyl ester (Formula 1a)

An Erlenmeyer flask was charged with 95 to 98% H$_2$SO$_4$ (495 ml) and cooled in an ice bath to 8° C. HNO$_3$ (47.5 ml at 50% prepared by adding 50 ml of 70% HNO$_3$ to 30 ml of water) was then added to the flask and the mixture was again cooled to 8° C. in the ice bath. Solid α-oxotricyclo[3.3.1.1$^{3,7}$]decane-1-acetic acid, methyl ester (Formula D)(100 grams, 0.45 moles) was slowly added to the mixture in portions over 30 to 60 minutes to maintain a temperature less than 28° C. The reaction mixture was stirred while cooling in the ice bath. Progress of the reaction was monitored by either thin layer chromatography (TLC) or high performance liquid chromatography (HPLC). For TLC, a silica gel was used and the solvent was EtOAc/MeOH/Hexane (9/1/10); KMnO$_4$. For HPLC, a 4.6×50 mm, C18, 3 micron, 120 angstrom column was used with a gradient of 10% acetonitrile/H$_2$O to 100% acetonitrile in 7 minutes at a flow rate of 2.5 ml/minute. The monitoring wavelength was 200 nm. When the reaction was complete (after approximately 1 hour), the reaction was quenched by addition to cold water (1.5 liters) and EtOAc (500 ml). Additional water and EtOAc (500 ml each) were added to aid in separation of the aqueous and organic layers. The aqueous layer was then extracted with 3 aliquots, 500 ml each, of EtOAc. The organic layers were combined and washed with brine (400 ml). The washed organic layer was then concentrated under reduced pressure to 130 grams of a yellow oil residue containing 3-hydroxy-α-oxotricyclo[3.3.1.1$^{3,7}$]decane-1-acetic acid, methyl ester (Formula 1a).

E. Hydrolysis of 3-hydroxy-α-oxotricyclo[3.3.1.1$^{3,7}$]decane-1-acetic acid, methyl ester (Formula 1a) to 3-hydroxy-α-oxotricyclo[3.3.1.1$^{3,7}$]decane-1-acetic acid (Formula 1)

The yellow oil residue of Part D was dissolved in tetrahydrofuran (300 ml) and cooled in a ice bath to 5° C. One liter of 1 N sodium hydroxide was added slowly to the solution to adjust the pH to approximately 7 while maintaining the temperature below 30° C. An additional 500 ml of 1N NaOH was then added to adjust the pH to approximately 14. The reaction mixture was then stirred while cooling in an ice bath and the progress was monitored by TLC or HPLC as described in Example 23. When the reaction was complete after approximately 30 minutes, EtOAc (500 ml) was added and the aqueous and organic layers were separated. The aqueous layer was washed with another 500 ml of EtOAc. The aqueous layer was acidified with concentrated HCl. When the solution reached pH 7, EtOAc (500 ml) was added followed by more concentrated HCl until the pH reached 0.7. Total concentrated HCl added was 150 ml. The aqueous layer was then extracted with EtOAc (4×400 ml) and the combined organic layers were washed with 400 ml of water followed by 400 ml of brine. The washed organic layer was then dried with MgSO$_4$ and concentrated. Yield was 88 grams of a light yellow solid. Dissolution of this solid in 100 ml EtOAc and 300 ml heptane with stirring for 30 minutes followed by filtration and air drying yielded 85 grams of a tan solid (85% 3-hydroxy-α-oxotricyclo[3.3.1.1$^{3,7}$]decane-1-acetic acid (Formula 1)).

E'. Preparation of 3-Hydroxy-α-oxotricyclo-[3.3.1.1$^{3,7}$]decane-1-acetic acid (Formula 1) employing a one pot procedure

1. Preparation of Dichloro-(3-hydroxy-adamantan-1-yl)-acetic acid methyl ester (Formula VIII)

Preparation of 10 N HNO$_3$: A 100 mL volumetric flask was charged with conc. HNO$_3$ (88.25 g, ~62.58 mL, ~1.0 mole) and cooled in an ice bath. Water (35 mL) was added. After the heat of mixing had dissipated, the solution was allowed to warm to room temperature. The flask was then made up to the mark with water to give 10 N HNO$_3$.

A 250 mL three-necked flask equipped with a thermocouple thermometer was charged with conc. H$_2$SO$_4$ (103 g, ~56 mL). After cooling to 0.4° C. in an ice bath, 10 N HNO$_3$ (5.68 mL, 56.8 mmol) was added over ~30 minutes. When the temperature of this acid mixture was lowered to ~1.0° C., the cold bath was removed. Adamantan-1-yl-dichloro-acetic methyl ester of formula VII (15.0 g, 54.11 mmol; ground lightly in mortar/pestle to break up large chunks/crystals) was added portionwise (1.25 g every 10 minutes; 1 hr 50 minute addition time). After ~5 hours the reaction mixture was a clear, pale yellow solution.

After stirring for ~24 hours the reaction mixture was a very pale yellow solution. A four-necked Morton flask (1 L) equipped with a mechanical stirrer and thermocouple thermometer was charged with water (250 mL) and urea (8.0 g, 0.133 mole, ~2.34 equivalents relative to HNO$_3$). To the resulting solution was added ethyl acetate (230 mL). Resulting biphasic mixture was cooled to ~1.0° C. in an ice bath. The reaction mixture from above was added, over ~15 minutes, to the cold EtOAc/water/urea mixture. The transfer was completed using additional ethyl acetate and water (~50 mL of each). After stirring for ~45 minutes, the cold bath was removed and the mixture was allowed to warm with stirring. After stirring for 4.5 hours (from start of quench), the resulting mixture was transferred to a separatory funnel (1 L) using additional ethyl acetate (~100 mL) to complete the transfer. The aqueous fraction was removed and extracted with ethyl acetate (1×80 mL). The organic fractions were combined and washed with water (2×90 mL), 1 N NaHCO$_3$ (4×90 mL), and brine. After drying over anhydrous magnesium sulfate, the solvent was removed at reduced pressure to give dichloro-(3-hydroxy-adamantan-1-yl)-acetic acid methyl ester of Formula VIII as a nearly colorless solid: 15.67 g (98.7% crude yield). This crude material can be used to prepare dichloro-(3-hydroxy-adamantan-1-yl)-acetic of Formula IX without purification. If desired, however, the crude material (15.65 g) can be recrystallized from methanol (102 mL) and water (85 mL) to afford a fluffy cotton-like solid (mp 114.8-115.0° C.) with 91% recovery.

Elemental analysis: $C_{13}H_{18}Cl_2O_3$:
Calculated: C, 53.25; H, 6.18; Cl, 24.18%.
Found: C, 53.24; H, 6.24; Cl, 24.31%.
$^1$H NMR (500.16 MHz, CDCl$_3$) δ 3.857 (s, 3H), 2.298 (br m, 2H), 1.824 (s, 2H), 1.793 (d, 4H, =2.75 Hz), 1.682, 1.629 (br AB q, 4H), 1.529 (m, 3H) ppm
$^{13}$C NMR (127.78 MHz, CDCl$_3$) δ 165.929, 94.281, 68.932, 54.150, 44.47 8, 44.529, 44.020, 35.750, 34.759, 30.149 ppm Lab HPLC:
YMC ODS-A S3 120 Å (4.6×50 mm), λ=200 nm, 2.5 ml/minute
Solvents: A=0.2% H$_3$PO$_4$ in water
B=90% CH$_3$CN in water
Gradient: 20% A to 100% B over 10 minutes

| Retention Time | Area % | Identity |
|---|---|---|
| 2.06 minutes | 1.19 | unknown |
| 4.54 minutes | 98.16 | dichloro-(3-hydroxy-admantan-1-yl)-acetic acid methyl ester |
| 5.09 minutes | 0.65 | unknown |
| 8.35 minutes | | adamantan-1-yl-dichloro-acetic methyl ester |

2. Preparation of 3-Hydroxy-α-oxotricyclo[3.3.1.1$^{3,7}$]decane-1-acetic acid

A 250-mL three-necked flask equipped with a pressure equating addition funnel and argon inlet was charged with dichloro-(3-hydroxy-adamantan-1-yl)acetic acid methyl ester (Formula VIII), prepared as described in Step 1 above (15 g, 51.16 mmol) followed by the addition of tetrahydrofuran (30 mL, instabilized). After stirring for several minutes, the bulk of the Formula VIII methyl ester dissolved to give a hazy solution. To this solution was added distilled water (30 mL) and a loose suspension formed. The addition funnel was charged with 1N NaOH (69 ml, 69 mmol, ~1.35 eq relative to Formula VIII compound input). NaOH was added dropwise over 70 minutes to give a nearly colorless solution which was allowed to stir at ambient temperature.

HPLC analysis at ~16 hours showed the hydrolysis of the Formula VIII compound complete. The reaction mixture, a clear colorless solution with a pH of 13.24, was adjusted to pH 7.40 by the addition of ~6NHCl (2.8 mL). Solid NaHCO$_3$ (11.2 g, 0.133 mol., 2.60 eq) was added to form a suspension.

HPLC analysis after heating for 4 hr 15 min shows the reaction to be complete. After heating for 5 hours, the heat source was removed and the reaction mixture (clear, colorless solution) was allowed to cool. After cooling to room temperature, the reaction mixture was stored in a refrigerator (+4° C.) for 4 days.

After storage in the cold for 4 days the reaction mixture was still a clear colorless solution and HPLC analysis shows little, if any, change upon storage. After warming to room temperature, the mixture (pH 7.77) was acidified to pH 0.20 by the careful addition of conc. HCl (11 mL required, CO$_2$ evolution; at pH ~1.40 a colorless solid began to precipitate). The resulting suspension was extracted with EtOAc (×4, ~500 mL total volume; HPLC analysis performed on aqueous fraction after each EtOAc extraction). The aqueous layer (pH 0.38) after the 1$^{st}$ EtOAc extraction was adjusted to pH 0.18 by the addition of conc. HCl (~1.6 mL required). The aqueous layer (pH 0.37) after the 2$^{nd}$ EtOAc extraction was adjusted to pH 0.17 by the addition of conc. HCl (~0.8 mL required). The aqueous layer required no additional pH adjustment after the remaining EtOAc extractions (extraction #3, pH 0.19; extraction #4, pH 0.19). The organic fractions were combined. After drying (MgSO$_4$), the solvent was removed at reduced pressure to give crude title Formula II compound as a nearly colorless, granular solid which was dried under vacuum (pump) for 16 hours: 11.42 g (99.53% yield); HPLC, 100% (area %).

Elemental analysis: C$_{12}$H$_{16}$Cl$_2$O$_3$ [55465-020-31, TR46373]
Calculated: C, 64.27%; H, 7.19%.
Found: C, 64.19%; H, 7.09%.

Crude Formula 1a compound (5.0 g) was dissolved with heating to ~85° C. in distilled water (19 mL), then removed from the heat source and allowed to cool. At ~53° C., the material began to crystallize. After standing at room temperature for ~2 hours, the solid was collected by filtration and washed with ice cold water. The bulk of the water was removed by pulling nitrogen through the filtercake. The material was then dried under vacuum (pump) for 17 hours to give title Formula 1a compound as large, colorless needles: 4.33 g (86.6% recovery); mp 164.5-165.6° C. (on Mettler FP800 system); HPLC, 100% (area %).

Elemental analysis: C$_{12}$H$_{16}$Cl$_2$O$_3$ [55465-023-15, TR46905]
Calculated: C, 64.27%; H, 7.19%.
Found: C, 64.42%; H, 7.04%.

F. Esterification of L-Pyroglutamic Acid (Formula E) to Form L-Pyroglutamic Acid Ethyl Ester (Formula F)

A reaction vessel was charged with ethanol (49.0 liters) and cooled to −5° C. The reaction vessel was then charged with thionyl chloride (4.97 kg) in a manner so that the temperature of the mixture did not exceed 0° C. After complete addition of the thionyl chloride, the mixture was cooled again to −5° C. and L-pyroglutamic acid (Formula E) was added portionwise so that the temperature was maintained between 0 and −5° C. during the addition. Following addition of the acid, the reaction mixture was heated to 20 to 25° C. and stirred for 5 hours. The reaction mixture was then evaporated under vacuum (T max 45° C.) to approximately 15% of its original volume. The remaining oil was then dissolved in toluene (49 liters). The toluene solution was then cooled to approximately 10° C. and triethyl amine (8.45 kg) was added slowly so that the maximum temperature was between 20 and 25° C. The resulting suspension was stirred for 30 minutes and then filtered. The filter cake was washed with toluene (about 5 liters). The filtrate was reduced at 50° C. under vacuum to a total volume of about 10 liters. Crystallization was initiated by slow addition of cyclohexane (8 liters) at 50° C. and subsequent cooling to approximately 30° C. After seed formation the mixture was cooled to 20 to 25° C. and charged with a second 8 liter portion of cyclohexane. The mixture was then cooled to 6 to 8° C., stirred for one hour, and the resulting crystals were filtered off. The crystals were washed twice with cyclohexane (4 liters each wash). The yield was 4.89 kg (82%) L-pyroglutamic acid ethyl ester (Formula F) as colorless needles.

G. BOC-Protection of L-Pyroglutamic Acid Ethyl Ester (Formula G)

The L-pyroglutamic acid ethyl ester (Formula F)(5.00 kg) was dissolved at room temperature in toluene (24.97 liters). 4-Dimethylaminopyridine (0.19 kg) was then added to the solution. The reaction mixture was then charged with a solution of BOC-anhydride (7.29 kg) dissolved in toluene (24.97 liters) in a manner so that the reaction temperature did not exceed 25° C. After complete addition, the reaction temperature was stirred for three hours at 25° C. The reaction mixture was then charged with half saturated NaHCO$_3$-solution (49.94 liters) and stirred vigorously for 10 minutes before separating the organic and aqueous phases. The separated organic layer was washed twice with water (24.97 liters each). The organic layer was then evaporated from solvent under vacuum at a maximum of 50° C. The remaining colorless to slight yellowish oil crystallized on standing. The theoretical yield was 8.18 kg, (31.81 mol) of the (5S)-2-oxopyrrolidine-1,5-dicarboxylic acid, 1-(1,1-dimethylethyl), 5-ethyl ester (Formula G).

H. SuperHydride Reduction and Elimination

The (5S)-2-oxopyrrolidine-1,5-dicarboxylic acid, 1-(1,1-dimethylethyl),5-ethyl ester (Formula G)(4.80 kg) was dissolved in toluene (30.97 liters; Kf max 0.01% water) and cooled to −50° C. This solution was charged with SuperHydride (LiEt$_3$BH 1 M in THF; 19.96 liters) in a manner so that the reaction temperature did not exceed −45° C. After complete addition, the mixture was stirred at −45 to −50° C. for 30 minutes. N-ethyldiisopropylamine (DIPEA; 14.47 liters) was then added to the reaction mixture in a manner so that the temperature did not exceed −45° C. Dimethyaminopyridine (0.030 kg) was added as a solid to the mixture. The reaction mixture was then charged with trifluoroacetic anhydride (TFAA) (4.70 kg) in a manner so that the reaction temperature did not exceed −45° C. After complete addition, the reaction mixture was warmed to 20 to 25° C. within one hour and kept for an additional 2 hours at this temperature. The reaction mixture was then cooled to 0° C. and slowly charged with water (48.00 liters) so that the reaction temperature did not exceed 5° C. Aqueous and organic phases were then separated and the organic phase was again washed with 48 liters of water (0 to 5° C.). The organic later was then evaporated and degassed at 40° C. A yellowish oil was obtained with a yield of 4.5 kg (18.66 mol, 100%) of the 4,5-dihydro-1H-pyrrole-1,5-dicarboxylic acid, 1-(1-dimethylethyl), 5-ethyl ester (BOC-DHPEE)(Formula G′).

I. Hydrolysis of BOC-DHPEE (Formula G′)

A solution prepared from 4,5-dihydro-1H-pyrrole-1,5-dicarboxylic acid, 1-(1,1-dimethylethyl),5-ethyl ester (BOC-DHPEE)(Formula G′)(6.00 kg) and ethanol (24.00 liters) was cooled to 0 to 5° C. and slowly treated at this temperature with a solution of lithium hydroxide hydrate (2.09 kg) in water (20.87 liters) to produce a turbid solution. This turbid solution was then warmed to 20 to 25° C. and stirred for 2 hours at this temperature. The reaction mixture was then evaporated to a volume of approximately 10.5 liters at a maximum temperature of 40° C. under vacuum and charged with water (24.00 liters) and t-butylmethyl ether(TBME or MTBE), (24 liters) and mixed for 10 minutes. The resulting organic and aqueous phases were separated and the aqueous phase was charged again with 24 liters of TMBE. This mixture was then cooled to 5 to 10° C., and the pH was adjusted to 2.3 to 2.3 using H$_3$PO$_4$ 85%-water (1:4) while being vigorously stirred. The temperature was maintained during this process at 5 to 10° C. for stability. The resulting organic and aqueous layers were separated. The organic layer was stored and the aqueous layer was again extracted with 24 liters of pre-cooled TBME at 5 to 10° C. The resulting organic layer was combined with the stored organic layer and charged with diisopropylethylamine (DIPEA) (4.82 kg). The solution was then evaporated and degassed at a maximum temperature of 30° C. under vacuum. The yield was 7.84 kg (22.88 mol, 92%) [N—BOC dehydroproline*DIPEA (BOC-DHP)].

J. Amide Formation on BOC-DHP

BOC-DHP, synthesized by saponification as described in Part I may contain water. Therefore an azeotropic distillation with toluene was applied prior to running the reaction. However, due to the excess of reagents, calculation of raw materials was based on the amount of BOC-DHP prior to removing any water. For azeotropic distillation, BOC-DHP was diluted with toluene to an approximate 30% solution. Toluene was removed under vacuum at 40° C. Treated BOC-DHP (6.00 kg) was then dissolved in THF (48.0 liters). The solution was charged with DIPEA (2.26 kg) and the reaction mixture was cooled to −20 to −25° C. Mesyl chloride (3.01 kg was then added slowly. During this addition, DIPEA hydrochloride precipitates. The resulting suspension was then stirred for 2 hours at −20° C. followed by saturation with ammonia via a sub-surface gas inlet. While adding the ammonia, the reaction was heated to 0° C. After saturation, the reaction mixture was heated to 20° C. and stirred for 3 hours. Following stirring, the reaction mixture was filtered to remove hydrochloride. The filter cake was washed with THF (12 liters) in several portions. The filtrate was concentrated under vacuum at a maximum temperature of 40° C. and then dissolved in methylene chloride (33.33 liters). The solution was washed with water (26.66 liters). The resulting organic and aqueous phases were separated and the aqueous phase was extracted twice with methylene chloride (20 liters each). The resulting organic layers were combined and concentrated under vacuum and degassed to remove any excess Hünigs base. The yield was 3.35 kg (15.77 mol, 90%) of (5S)-5-aminocarbonyl-4,5-dihydro-1H-pyrrole-1-carboxylic acid, 1-(1,1-dimethylethyl) ester (BOC-DHPA)(Formula G″).

K. Cyclopropanation of (5S)-5-aminocarbonyl-4,5-dihydro-1H-pyrrole-1-carboxylic acid, 1-(1,1-dimethylethyl)ester (Formula G″)

A first reactor, Reactor A, was charged with BOC-DHPA (Formula IV)(4 kg) dissolved in methylene chloride (18.0 liters) and maintained at 20° C. A second reactor, Reactor B, was charged with methylene chloride (18.00 liters) and cooled to −30° C. Reactor B was then charged with dimethoxy ethane (DME) (3.36 kg), followed by a 30% solution of diethyl zinc (15.36 kg) in toluene, while maintaining the temperature between −30 and −25° C. Reactor B was then charged with diiodo methane (19.99 kg) while maintaining the reaction temperature between −30 and −25° C. After complete addition of the diiodo methane, the mixture was stirred for 45 minutes at −30 to −25° C. This mixture was then charged to Reactor A via a cooled pipe (−20 to −25° C.). Charging was performed slowly in portions of approximately 5% so that the reaction temperature of Reactor A was maintained between 22 and 24° C. until the reaction was completed. Following completion of the reaction, the mixture of Reactor A was cooled to 5 to 10° C. The reaction mixture was then slowly charged with saturated bicarbonate solution (21.6 liters) in a manner so that the reaction temperature did not exceed 15° C. Following this addition, the reaction mixture was stirred for at least one hour while a precipitate formed. The suspension was filtered. The resulting filter cake was transferred back to the vessel, slurried again with methylene chloride (14.4 liters) for 30 minutes; and re-filtered. Following this second filtration, the filter cake was washed with addition methylene chloride (7.2 liters). The filtrates were then separated into aqueous and organic phases and the organic phase was washed with half saturated brine (21.6 liters). Solvent was then removed by vacuum at a maximum temperature of 30° C. and exchanged by heptane. A slurry of crude product in heptane was obtained. Final volume of the suspension after solvent exchange was 14.4 liters. The crude product was isolated by filtration. The filtercake was washed with heptane (2.9 liters) and then dried under vacuum to a constant weight. The crude yield was 2.76 kg (12.2 mol, 72%) [1S-(1α,3β,5α]-3-aminocarbonyl)-2-azabicyclo[3.1.0]hexane-2-carboxylic acid, 1,1-dimethylethyl ester (Formula H). To purify, the crude material is slurried in 8-fold amount of a 1:1 mixture of butyl acetate/heptane at 20 to 22° C. for 4 hours. The material was filtered and the filtercake was washed with an approximate 1-fold amount of heptane. The yield was 2.11 kg (9.33 mol, 55%) [1S-(1α,3β,5α)]-3-aminocarbonyl)-2-azabicyclo[3.1.0]hexane-2-carboxylic acid, 1,1-dimethylethyl ester (Formula H).

L. Deprotection of [1S-(1α,3β,5α)]-3-(aminocarbonyl)-2-azabicyclo[3.1.0]hexane-2-carboxylic acid, 1,1-dimethylethyl ester (Formula H) to form (1S,3S,5S)-2-azabicyclo[3.1.0]hexane-3-carboxamide (Formula J)

A 100 ml, 2 necked flask equipped with a mechanical stirrer and a thermocouple was charged with [1S-(1α,3β,5α)]-3-aminocarbonyl)-2-azabicyclo[3.1.0]hexane-2-carboxylic acid, 1,1-dimethylethyl ester (Formula H)(5.0 grams, 22.1 mmol) and THF (20 ml). HCl (2.5 M in EtOAc, 25 ml, 62.5 mmol) was then added to the suspension. The resulting solution was stirred at room temperature for 18 hours during which time precipitation was observed. Completion of the reaction was monitored by HPLC. Methyl t-butyl ether (MTBE) (30 ml) was added to the suspension and stirring was continued for an additional 30 minutes. The suspension was then filtered under $N_2$ protection to produce a white solid that was washed with MTBE (20 ml). The solid was dried in an oven under reduced pressure for 48 hours to afford the hydrochloride salt of (1S,3S,5S)-2-azabicyclo[3.1.0]hexane-3-carboxamide (Formula J; 3.6 grams, 100%).

M. BOC Protection of (αS)-α-amino-3-hydroxytricyclo[3.3.1.1$^{3,7}$]decane-1-acetic acid (Formula 2) to form (αS)-α[[(1,1-dimethylethoxy) carbonyl]amino]-3-hydroxytricyclo[3.3.1.1$^{3,7}$]decane-1-acetic acid, Formula 3 Acid A preferred method of preparing the free acid (Formula 3) is described in Example 3. Alternatively, the following method can be used to make the free acid (αS)-α-amino-3-hydroxytricyclo[3.3.1.1$^{3,7}$]decane-1-acetic acid (Formula 2) (469 grams, 2.08 moles) was dissolved in ice cold 1 N NaOH (5 liters, 5 moles, 2.4 equivalents) in a phase splitter equipped with a temperature probe and a pH probe. THF (2.5 liters) was added to the solution. Solid $Boc_2O$ was then added and the reaction mixture was stirred at ambient temperature for approximately 1 hour. EtOAc (4 liters) was then added with stirring and the resulting organic and aqueous layers were separated. The pH of the aqueous layer was adjusted to 7 with concentrated HCl. EtOAc (4 liters) was then added and additional HCl was added to lower the pH to approximately 1. The total volume of concentrated HCl added was 510 ml. The organic and aqueous layers were again separated and the aqueous layer was extracted with EtOAc (3×3 liters). The organic layers were then combined and washed with water (3 liters) and brine (3 liters). The washed organic layer was then dried with $Na_2SO_4$ and concentrated on a rotovap at room temperature until dryness. The yield was 542 grams of (αS)-α[[(1,1-dimethylethoxy)carbonyl]amino]-3-hydroxytricyclo[3.3.1.1$^{3,7}$]decane-1-acetic acid (Formula 3).

N. Coupling Reaction to produce 3-cyano-(αS)-α-(3-hydroxytricyclo[3.3.1.1$^{3,7}$]dec-1-yl)-(3-oxo-(1S,3S,5S)-2-azabicyclo[3.1.0]hexane-2-ethanecarbamic acid, 1,1-dimethylethyl ester (Formula K)

A 2 L three-necked flask equipped with a thermometer, a mechanical stirrer and a gas inlet was charged with (αS)-α [[(1,1-dimethylethoxy)carbonyl]amino]-3-hydroxytricyclo[3.3.1.1$^{3,7}$]decane-1-acetic acid (Formula 3) (50 grams, 153.8 mmol). THF (200 ml) was added and stirred to produce a clear solution. The solution was cooled to −6° C. in an acetone-dry ice-water bath. Methanesulfonyl chloride (Mes-Cl)(13.1 ml, 169 mmol, 1.1 equivalents) was then added as a single portion followed by diisopropylethylamine (94 ml, 539 mmol, 1.1 equivalents). The diisopropylethylamine was added slowly over a period of about 4 minutes to keep the internal temperature below 8° C. The reaction mixture was stirred at 0° C. until all acid was converted to mixed anhydride. (1S,3S,5S)-2-azabicyclo[3.1.0]hexane-3-carboxamide hydrochloride salt (32.5 grams, 200 mmol, 1.1 equivalents) and hydroxybenzotriazole (HOBT) (1.04 grams, 7.6 mmol, 0.05 equivalents) were then added in a single portion and the flask was removed from the cooling bath. The reaction mixture was stirred at room temperature for 2 hours and then left overnight at room temperature.

O. Dehydration and Hydrolysis to Produce 3-cyano-(αS)-α-(3-hydroxytricyclo[3.3.1.1$^{3,7}$]dec-1-yl)-β-oxo-(1S,3S,5S)-2-azabicyclo[3.1.0]hexane-2-ethanecarbamic acid, 1,1-dimethylethyl ester (Formula L)

Pyridine (6 equivalents, 922 mmol, 74.6 ml) was added to the reaction mixture of Part N and the reaction mixture was cooled in a cooling bath to −8° C. Trifluoroacetic anhydride (TFAA) (4 equivalents, 616 mmol, 87 ml) was then added slowly over 6 minutes while keeping the temperature below 10° C. The reaction was stirred at 24° C. for 0.5 h and checked via HPLC (30 ml, 0.5 ml AcN, 0.5 ml $H_2O$) for the disappearance of Part N Compound K.

The reaction was then cooled in a cooling bath to approximately −3° C. NaOH (5 N, 6 equivalents, 0.925 mol, 185 ml) was added to the reaction over 10 minutes (aqueous pH=9.9) while maintaining the reaction temperature below 10° C. Aqueous $K_2CO_3$ (319 grams, 15 equivalents, dissolved in 510 ml $H_2O$) was added over 5 minutes (temperature=8° C., aq. pH 11.1). The reaction was allowed to run for 7 hours 40 minutes. The reaction was complete when all intermediates were hydrolyzed to penultimate as determined via HPLC (30 µl, 0.5 ml AcN, 0.5 ml $H_2O$).

EtOAc (500 ml) was then added to the reaction mixture and the resulting aqueous and organic layers were separated. The organic layer was washed with 500 ml buffer solution (2M $H_3PO_4$, 1M $NaH_2PO_4$). The temperature rose to 23° C. from 15° C.; addition time: 5 min., aq. V=560 ml pH=4.5, 32 mg product by HPLC; org V=1,080 ml. The organic was washed with a second 500 ml buffer solution; aq. V=780 ml, pH=2.5, 415 mg product by HPLC; organic V=800 ml, 1.02 v/v % pyridine. The organic was washed with 300 ml brine; aq. V=350 ml, pH=1.8, 20 mg produced by HPLC. The organic was washed with 130 ml sat. $NaHCO_3$ solution; aq. V=176 ml, pH=6.0, 780 mg product. The organic was washed with 300 ml half sat. brine; aq. V=330 ml, pH=5.2, 25 mg product; organic V=650 ml, pyridine 0.045 v/v %. 5 g Darco was added to the organic and stirred for 5 min, filtered through 50 g silica, washed with 4×25 ml EtOAc, organic V=750 ml, pyridine 0.04 v/v %.

The organic layer was then distilled to approximately 133 ml. The organic was stirred for 1 hour until the solution turned cloudy. 133 ml heptane was added over 15 min. and the slurry stirred overnight. 133 ml heptane was added overnight. The mixture was stirred violently for 20 minutes with mechanical stirring. The solids were filtered off and the cake was washed with 50 ml 5% EtOAc/heptane; 3.4 g product was found in 8.86 g crude after removal of solvents from the mother liquor.

Dry product crystals were heated at 50° C. under vacuum overnight. 467 g product was obtained ~73%, 96.6 AP.

P. Deprotection to produce (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1)(Formula M)

3-cyano-(αS)-α-(3-hydroxytricyclo[3.3.1.1$^{3,7}$]dec-1-yl)-β-oxo-(1S,3S,5S)-2-azabicyclo[3.1.0]hexane-2-ethanecarbamic acid, 1,1-dimethylethyl ester (Formula L)(5.0 grams, 12.04 mmoles) was charged to a three-necked flask equipped with a thermometer, a mechanical stirrer, and a gas inlet. EtOAc, approximately 45 to 50 ml, was added to achieve a clear solution. Concentrated HCl (3.00 ml, 37% w/w %, 36.14 mmoles, 3 equivalents) was added at room temperature and the reaction mixture was stirred until a solid was produced. Water (30 ml) was then added and the mixture was stirred for 1 to 2 minutes. This reaction mixture was transferred to a separatory funnel and the layers of the reaction mixture were allowed to separate into a clean phase split. The aqueous layer was adjusted to a lower pH of approximately 6 with 25% NaOH while maintaining the temperature below 25° C.

Salt exchange was then performed by addition of isopropyl alcohol (IPA; 2 to 3 ml) to the aqueous layer followed by addition of sodium benzoate (0.65 ml of a sodium benzoate solution prepared by dissolving 2.6 grams for sodium benzoate in 6.5 ml of water). The remaining sodium benzoate solution was then added in dropwise fashion via an addition funnel. The resulting reaction mixture was stirred at room temperature for 16 to 24 hours. Solids in the reaction mixture were then filtered on a Buchner funnel and washed with water until the solid gave a negative test for Cl— with AgNO$_3$. The solids were then washed with heptane (10 ml) to drive off the water, air dried on the funnel, an dried in a vacuum oven at 35° C. until KF≦5%. Yield was 79%, 4.1 grams.

Q

Deprotection of L

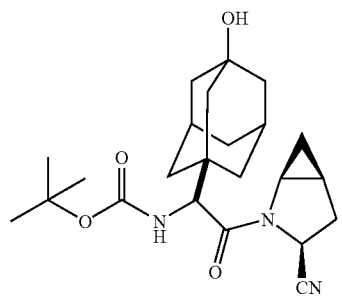

L to produce free base M'

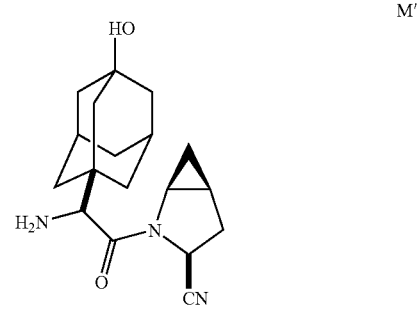

M'

Part O compound (L) (300 g, 0.723 mol, potency of 90.6%), methylene chloride (3 L), methanol (288 ml, 7.23 mol) and concentrated (36%) hydrochloric acid (288 ml, 7.23 mol) were charged to a 3-neck 12 L flask equipped with mechanical stirrer, temperature probe and N$_2$ gas inlet. Reaction occurred while maintaining reaction temperature within the range from about 20 to about 25° C. The reaction mixture was stirred for 18 hours, split into 2 phases and the top aqueous layer was collected. To the aqueous layer was added methylene chloride (6 L), and water (720 ml), and 5N NaOH (~600 ml) was added dropwise to adjust pH to 9.0~10.5.

The organic phase containing the hydrochloric salt

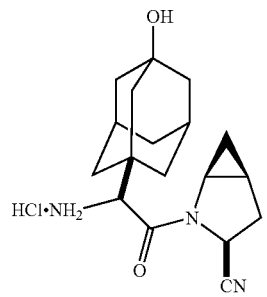

(identified by HPLC) (Formula L') was treated with methylene chloride (6 L) and water (720 ml), and 5N sodium hydroxide solution (~600 ml) was added dropwise while maintaining reaction temperature between 20 and 25° C. to adjust pH between 9 and 10.5. NaCl (120 g) was added and the mixture agitated for 20 min. to form a phase split. The organic layer (6.2 L) was collected (contained ~174 g of compound M') and the aqueous layer (1.75 L) was discarded (contained 6.5 g compound M').

The organic layer was washed with 1% NH$_4$Cl brine solution (450 ml). (1% NH$_4$Cl brine solution contained 1 g NH$_4$Cl, 25 g NaCl and 74 g H$_2$O). From the resulting phase split 6.0 L organic layer was recovered (contained ~176 g compound M' in solution) and the aqueous layer (0.45 L) containing 1.4 g compound M' (~0.4%) was discarded.

Ethyl acetate (~4 L) was added to the organic layer while CH$_2$Cl$_2$ was distilled off at 25° C./50 mm Hg. Distillation was discontinued when a final volume of 2.5 L was reached. The organic layer was polish filtered to remove solid NaCl and was concentrated to ~1 Kg (~170 g of compound M' in 1 L ethyl acetate) GC analysis: DCM<0.1%. Water (17 ml) was added dropwise and after 10 min. crystallization began. 17 ml of water was added and the resulting slurry was agitated for 30 min, filtered, the cake washed with ethyl acetate and dried at rt under vacuum to give 186 g of compound M', yield 81%.

What is claimed is:

1. A process for preparing the compound of Formula 2

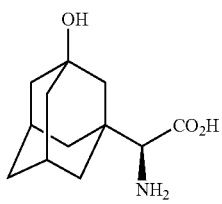

Formula 2 which comprises treating an aqueous solution of the compound of Formula 1

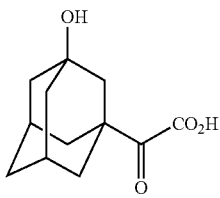

Formula 1 with ammonium formate, nicotinamide adenine dinucleotide, dithiothreitol and partially purified phenylalanine dehydrogenase (PDH) and/or formate dehydrogenase (FDH) enzyme concentrate to provide the compound of Formula 2.

2. The process as defined in claim 1 wherein the partially purified phenylalanine dehydrogenase and/or formate dehydrogenase enzyme concentrate is prepared by a method comprising:

(a) preparing a fermentation broth containing a microorganism capable of producing PDH and/or FDH;
(b) microfluidizing the fermentation broth while maintaining the temperature of said fermentation broth between about 4° C. and 30° C. to form a microfluidized broth containing the PDH and/or FDH;
(c) clarifying the microfluidized broth by treating the broth with aflocculating agent to coagulate cell debris and remove DNA and unwanted proteins, thereby forming a clarified broth;
(d) filtering the clarified broth to give a filtrate; and
(e) concentrating the filtrate to give said partially purified enzyme concentrate, the concentrate containing:
  (i) said PDH having a PDH activity of about 400 IU/mL to about 1000 IU/mL; and/or
  (ii) said FDH having a FDH activity of about 20 IU/mL to about 200 IU/mL.

3. The process as defined in claim 1 wherein the aqueous solution is warmed to about 35° C. to about 40° C.

4. The process as defined in claim 3 wherein the treating further comprises maintaining the aqueous solution at a pH of about 7.0 to about 8.6.

5. The process as defined in claim 4 wherein the pH is maintained with NaOH.

6. The process as defined in claim 5 wherein the treating comprises reacting the aqueous solution for a period of time from about 24 hours to about 48 hours.

7. A process for preparing the compound of Formula 3

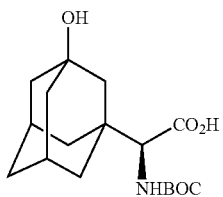

Formula 3 which comprises
(a) treating an aqueous solution of the compound of Formula 1

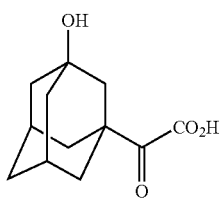

Formula 1 with ammonium formate, nicotinamide adenine dinucleotide, dithiothreitol and partially purified phenylalanine dehydrogenase and/or formate dehydrogenase enzyme concentrate; and
(b) treating the aqueous solution of step (a) with di-tert-butyl dicarbonate to provide the compound of Formula 3.

8. The process as defined in claim 7 wherein the treating in step (b) further comprises maintaining the aqueous solution at a pH of about 8.5 to about 12.5.

9. The process as defined in claim 7 further comprising isolating the compound of Formula 3.

10. The process as defined in claim 9 further comprising crystallizing the isolated compound of Formula 3.

11. The process as defined in claim 7 wherein the partially purified phenylalanine dehydrogenase and/or formate dehydrogenase enzyme concentrate is prepared comprising:
(a) preparing a fermentation broth containing a microorganism capable of producing PDH and/or FDH;
(b) microfluidizing the fermentation broth while maintaining the temperature of said fermentation broth between about 4° C. and 30° C. to form a microfluidized broth containing the PDH and/or FDH;
(c) clarifying the microfluidized broth by treating the broth with a flocculating agent to coagulate cell debris and remove DNA and unwanted proteins, thereby forming a clarified broth;
(d) filtering the clarified broth to give a filtrate; and
(e) concentrating the filtrate to give said partially purified enzyme concentrate, the concentrate containing:
  (i) said PDH having a PDH activity of about 400 IU/mL to about 1000 IU/mL; and/or
  (ii) said FDH having a FDH activity of about 20 IU/mL to about 200 IU/mL.

12. The process as defined in claim 2 wherein the enzyme concentrate is capable of reductively aminating a keto-containing compound into a chiral amine-containing compound; wherein said chiral amine-containing compound, without isolation from the enzyme concentrate, is capable of being BOC-protected; and wherein, optionally, the clarifying comprises contacting the microfluidized broth with diatomaceous earth and the filtering comprises filtering the diatomaceous earth with a filter press.

13. The process as defined in claim 2 wherein in step (b) the microfluidizing comprises providing a pressure from about 12,000 to about 20,000 psi.

14. The process as defined in claim 2 wherein in step (b) the temperature of the fermentation broth is maintained between about 4° C. and 25° C.

15. The process as defined in claim 2 wherein in step (b) the temperature of the fermentation broth is maintained between 8° C. and 25° C.

16. The process as defined in claim 2 wherein the PDH is obtained from a microorganism selected from the group consisting of the genera *Sporosarcina* or *Thermoactinomyces*.

17. The process as defined in claim 2 wherein the PDH is obtained from *Thermoactinomyces intermedius*.

18. The process as defined in claim 2 wherein the PDH is a *Thermoactinomyces intermedius* ATCC 33205 PDH expressed in *Escherichia coli* and the FDH is a *Pichia pastoris* ATCC 20864 FDH expressed in *Escherichia coli*.

19. The process as defined in claim 2 wherein the microorganism is *Escherichia coli* JM110.

20. The process as defined in claim 2 wherein in step (d) the filtering comprises ultrafiltering the clarified broth through an ultrafiltration membrane or cassette.

* * * * *

UNITED STATES PATENT AND TRADEMARK OFFICE
CERTIFICATE OF CORRECTION

PATENT NO. : 8,222,009 B2  
APPLICATION NO. : 12/817370  
DATED : July 17, 2012  
INVENTOR(S) : Politino et al.

It is certified that error appears in the above-identified patent and that said Letters Patent is hereby corrected as shown below:

In the Claims

In Claim 2, at Column 43, Line 8 "aflocculating" should be replaced with "a flocculating".

Signed and Sealed this  
Thirteenth Day of May, 2014

Michelle K. Lee  
*Deputy Director of the United States Patent and Trademark Office*

SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: Oligonucleotide primer containing the 5' and
      3' end of the P. pastoris FDH gene

<400> SEQUENCE: 1
tcgtcatgaa aatcgttctc gttttg                                    26

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide primer containing the 5' and
      3' end of the P. pastoris FDH gene

<400> SEQUENCE: 2
tactgttttt ccagcgtatt cctaggct                                  28

<210> SEQ ID NO 3
<211> LENGTH: 33
<212> TYPE: DNA
<213> ORGANISM: Artificial Sequence
<220> FEATURE:
<223> OTHER INFORMATION: Oligonucleotide primer containing 5' and 3'
      end of the PDHmod gene

<400> SEQUENCE: 3
gatgctcata tgcgcgacgt gtttgaaatg atg                            33

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide primer containing 5' and 3'
      end of the PDHmod gene

<400> SEQUENCE: 4
gatcccgggc taaggcgaat taataattcg                                30